United States Patent [19]
Baust et al.

[11] Patent Number: 6,045,990
[45] Date of Patent: Apr. 4, 2000

[54] INCLUSION OF APOPTOTIC REGULATORS IN SOLUTIONS FOR CELL STORAGE AT LOW TEMPERATURE

[76] Inventors: John M. Baust, 176 Ralsh Hill Rd., Candor, N.Y. 13743; Robert G. Van Buskirk, 1320 W. Glann Rd., Apalachin, N.Y. 13732; John G. Baust, 175 Ralsh Hill Rd., Candor, N.Y. 13743; Mathew Aby, 22 Edgewood Rd., Binghamton, N.Y. 13903

[21] Appl. No.: 09/283,756

[22] Filed: Apr. 2, 1999

Related U.S. Application Data

[60] Provisional application No. 60/092,239, Jul. 9, 1998.
[51] Int. Cl.$^7$ .............................. A01N 1/02; C12Q 1/68
[52] U.S. Cl. ............................ 435/1.1; 435/1.2; 435/1.3; 435/6; 435/325
[58] Field of Search .............................. 435/1.1, 1.2, 1.3, 435/325, 6

[56] References Cited

U.S. PATENT DOCUMENTS

| | | | |
|---|---|---|---|
| 5,405,742 | 4/1995 | Taylor | 435/1.1 |
| 5,514,536 | 5/1996 | Taylor | 435/1.1 |
| 5,635,187 | 6/1997 | Bathurst et al. | 424/195.1 |

OTHER PUBLICATIONS

Taylor et al., "A New Solution for Life Without Blood . . . ", Circulation, vol. 91, No. 2 (Jan. 15, 1995), pp. 431–444.

Cook et al., "Cold–Storage of Synthetic Human Epidermis in Hypo Thermosol", Tissue Engineering, vol. 1, No. 4 (1995), pp. 361–377.

Kerr et al., Apoptosis: A Basic Biological Phenomenon With Wide–Ranging Implications in Tissue Kinetics, Br. J. Cancer, No. 26, (1972), pp. 239–257.

Van Buskirk et al., "Assessment of Hypothermic Storage of Norman Human Epidermal Keratinocytes (NHEK) Using Alamar Blue", In Vitro Technology, vol. 9, No. 3 (1996), pp. 297–303.

Southard, et al., "Organ Preservation", Amer. Rev. Med., vol. 46 (!995), pp. 235–247.

Baust, John G., "Concepts in Cryopreservation", Fisher Scientific BioTrack, vol. 4, No. 1 (1989), pp. 1–2.

Descotes et al., "Cryopreservation of Organs: NMR Follow–up of Cryoprotectant Perfusion in Rabbit Kidneys", Transplantation Proceedings, vol. 25, No. 1 (1996), pp. 346–348.

*Primary Examiner*—James Ketter
*Attorney, Agent, or Firm*—Pillsbury Madison & Sutro LLP

[57] ABSTRACT

Cell-free solution compositions for hypothermic cell storage supplemented with agents inhibiting apoptotic induced cell death are provided for chill preservation of cells at about 0° C. to about 10° C. Additionally, solutions for cell storage at hypothermic temperatures supplemented with cell death inhibitors for cryopreservation are disclosed. Methods for use of these solutions are described.

12 Claims, 14 Drawing Sheets

INCLUSION OF APOPTOTIC REGULATORS IN SOLUTIONS FOR CELL STORAGE AT LOW TEMPERATURE

This application claims the benefit of U.S. Provisional application Ser. No. 60/092,239 filed Jul. 9, 1998.

BACKGROUND OF THE INVENTION

1. Field of the Invention

The invention relates to chill preservation and cryopreservation compositions which control the induction of apoptosis in preserved cells. Particularly, the invention relates to methods of preserving cells, tissues and organs at hypothermic temperatures utilizing intracellular-type hypothermic maintenance and preservation media compositions containing reagents which control the induction of gene regulated cell death (apoptosis). The invention further relates to methods of cryopreserving cells with an intracellular-type hypothermic maintenance and preservation composition containing reagents which control the induction of apoptosis in preserved cells.

2. Description of Related Art

Non-blood based solutions useful for preserving organs, tissues and cells are well-known in the art. For example, blood substitutes for preserving tissues and organs for transplantation are disclosed by U.S. Pat. No. 4,920,044 to Breton and U.S. Pat. Nos. 4,879,283 and 4,798,824 to Belzer. U.S. Pat. No. 4,923,422 to Segall et al discloses a four solution blood substitute useful in hypothermic preservation of isolated organs for use in transplantation procedures. Typically, cold storage of human tissues at 4° C. in a conventional preservation solution results in cellular debris collecting in the culture medium surrounding the tissue samples within the first several days of storage. Many cells shrink after a few days at 4° C. and display ultrastructural damage. These cells and their tissues are not viable after cold-storage as a result.

Hypothermic storage solutions have been developed for shipping and storing organs, tissues and cells. Cells are immersed in these solutions and kept at or near 4° C., where they remain in a state of prolonged hypothermia. The growing number of engineered tissues has increased scientific interest in developing solutions for cold-store tissues at 4° C. on a short-term basis, but without the use of cryopreservation. Cold storage or hypothermic solutions, such as VIASPAN® [also called University of Wisconsin (UW) solution], EURO-COLLINS and others that have been used for organ storage (1), are now being tested for their abilities to keep cells and tissues in a state of hypothermia.

The importance of optimizing a cold-storage solution for cell/tissue storage cannot be overstated. Pahernik et al. (2) has noted the importance of large-scale stocking facilities for hepatocytes to develop bioartificial livers. This group points to chill preservation solutions as a milder alternative to cryopreservation since cryopreservation often results in a major loss of cell function. Fisher et al. (3) have tested VIASPAN®, EURO-COLLINS, Sacks+prostacyclin and V-7 for their abilities to cold-preserve tissue slices. The use of these chill preservation solutions for tissue slice preservation at temperatures between 5° C. and 0° C. would effectively increase the shipping/storage life of tissue sections, thereby decreasing the number of animals used in cosmetic and pharmaceutical testing. Another hypothermic solution developed by Taylor et al. (4) has been shown to protect engineered human epidermis at 4° C. for over a week (5). This bioartificial skin produced by MatTek Corporation (Ashland, Mass.) continues to differentiate at 37° C. after a week in an intracellular-like hypothermic blood substitute solution, HYPOTHERMOSOL®, at 4° C. Chill preservation of single cells has also been investigated by several groups For example, normal human epidermal keratinocytes can be maintained for periods exceeding one week at 4° C. in HYPOTHERMOSOL® versus only 24 hours in normal growth media (10). Similar results were obtained following the hypothermic storage of EPIDERM®, an engineered human epidermis used in product safety testing (5).

Hypothermic preservation solutions such as UW solution have been used for the preservation of heart (11–13), liver (1–16), lung (17–19), kidney (20), and small intestine (21). These procedures have been recently extended to the area of in vitro toxicology. Fisher et al. (3) have shown the importance of storing living liver and kidney slices used as animal alternatives in hypothermic preservation solutions. Cook et al. (5) have shown that HYPOTHERMOSOL® can be used for the cold-storage of engineered human epidermis at temperatures between 5° C. and 0° C. This observation is important because HYPOTHERMOSOL® could extend the shelf life of bioartificial human epidermis used as an alternative to animal testing. Alternatively, HYPOTHERMOSOL® or an alternative solution could be used to store human epidermis prior to grafting in clinical cases. While bioartificial livers are not currently in use, Pahernik et al, (2) has pointed, nonetheless, to the importance of banking liver cells for liver tissue engineering. However, the effectiveness of current chill preservation solutions is limited by cellular processes including gene regulated events which promote cell death during cold storage.

While cold storage of cells and tissues at about 5° C. to 0° C. is suitable for short periods of time, long-term storage of cells requires cryopreservation at temperatures between the onset of freezing and the temperature of liquid nitrogen (–196° C.). Cryopreservation, the maintenance of biologics including numerous cell lines at or near liquid nitrogen temperature, is a critical methodology necessary to support biomedical research. Preservation protocol development has focused on overcoming freeze-induced cell death due primarily to intracellular ice formation and chemo-osmotic stress, which result in plasma membrane disruption and subsequent necrosis (43). Accordingly, numerous investigators have cryopreserved cellular systems in cryoprotective agents, such as dimethyl sulfoxide (DMSO) or glycerol, contained in an extracellular-like carrier solution such as standard cell culture media. This strategy was first described following the partial preservation of bovine spermatozoa (44). Subsequently, numerous investigators have cryopreserved red blood cells (45), white blood cells (41), gametes and embryos (34), and simple tissues including heart valves (32) with limited success.

Traditional approaches to cryopreservation rely on the addition of molar concentrations of penetrating cryoprotectants contained in either isotonic or hypotonic media. This approach rarely considers the ionic balance, buffering capacity or other factors thought to be necessary to avoid the consequences of hypothermic stress. This situation may be problematic in view of the fact that cells during slow cooling (~1° C. min$^{-1}$) remain in a hypothermic state until the intracellular contents vitrify during liquid nitrogen (LN$_2$) quenching step of the preservation protocol. Post-thaw viability of cells is low using traditional methodology, such as freezing cells in solutions of culture media diluted with 5% to 10% DMSO. A post thaw survival rate of only about 30% of a frozen cell population is common when traditional protocols are followed. The high loss of cell viability after thawing is thought to be due to crystal formation and cellular dehydration that occurs during freezing.

The majority of investigators have assessed viability within a few hours of thawing using dye exclusion assays but provide little information on long term survival (3,27). For example, human hepatocytes assessed using a trypan blue dye exclusion assay yield approximately 67% survival following 24 hour storage but only 49% after 14 days storage at −80° C. (29). More recently, Adams et al. (26) have shown that hepatocyte preservation outcome can be improved by utilizing VIASPAN® (an intracellular-like, hypothermic storage solution) as the carrier solution fortified with fetal bovine serum and DMSO.

Nagle et al. (40) presented evidence suggesting that a molecular-based mode of cell death was associated with hypothermic storage and that cell death could not be accounted for by solely addressing the known mechanisms of chill-induced cellular injury. Parks (42) noted that the extent of hypothermic exposure experienced by cells during the preservation process appears to be a major factor affecting the success of cryopreservation. Recently, it has been reported that apoptotic cell death occurs in cardiomyocytes as a result of hypothermic exposure (39). Apoptosis, or programmed cell death, is a gene-activated event that occurs as a normal consequence of development (37), as well as a result of cellular stress (30). Hollister et al. (36) demonstrated that apoptosis is a significant component of cell death in a human prostate cancer cell line (PC3) exposed to subfreezing temperatures as low as −75° C. These data point to apoptosis as a possible contributing factor in cryopreservation failure.

Cell death may occur through apoptosis or necrosis (for a review see 24). Necrosis or pathological cell death is characterized by the loss of cell membrane integrity resulting in cell swelling and is caused by a number of pathological agents. DNA in cells that undergo necrosis is cleaved in a random fashion. Thus, the DNA from cells that have undergone necrosis appears as a continuous smear when subjected to gel electrophoresis. Apoptosis, is gene activated and is characterized by shrinking cells, intact plasma membranes, and the formation of apoptotic bodies. DNA in cells undergoing apoptosis is cleaved in a non-random fashion, forming a ladder-like pattern upon gel electrophoresis. The principal mode of cell death for many cells stored under hypothermic conditions for periods longer than 1–2 days in conventional preservation solutions appears to be necrosis, not apoptosis. The relationship between short term storage cold-storage and apoptosis is unclear.

The precise cellular mechanisms regulating apoptosis are not completely known. However, many portions of the apoptotic pathway have been delineated to date. Alteration of the ionic environment may be necessary to activate or inhibit the endonucleases relevant to the process of apoptotic nuclear degradation. For example, physiologic concentrations of $Zn^{++}$ are known to inhibit DNA fragmentation and apoptosis. Treatment of certain cells with inhibitors of macromolecular synthesis, such as actinomycin to block RNA synthesis or cyclohexamide to block protein synthesis, induces apoptosis. Completion of the apoptotic process appears to depend upon the regulated expression of various gene products associated with the promotion or suppression of gene activated cell death, particularly gene products involved with cell cycle regulation. For example, overexpression of the cell-death inhibiting agents Bcl-2 and Bcl-xL prevents the release of cytochrome C. Cytochrome C is thought to activate the caspases, a group of proteases known for cleaving substrates responsible for the changes associated with apoptosis. Enhanced levels of Bax, a pro-apoptotic member of the Bcl-2 family, promotes cytochrome C release and subsequent apoptosis of cells. Specific regulation of the early response genes c-myc, c-jun and c-fos may promote either cell growth or cell death, depending upon the circumstances surrounding their expression. Thus, programmed cell death involves an intricate cascade of cellular events.

The cold-storage efficacy of numerous cell preservation solutions has been examined using a plethora of assays. Such assays include enzyme synthesis (2), potassium content (3), trypan blue exclusion (7), neuronal outgrowth and myelination (8), contraction (11), ATP content (13), and ultrastructure (17). As pointed out previously (10), these assays can be considered either viability or functional assays. Thus, the maltose tolerance test used by Katz et al. (21) on the small intestine could be considered a functional assay; whereas the trypan blue test used by Rodriguez et al. (7) is strictly a viability assay. The ALAMAR BLUE™ assay used in the course of the study reported herein is a viability assay and does not indicate whether or not test cells are functioning in a tissue specific manner. Yet one of the key attributes of the ALAMAR BLUE™ assay that is not shared by most of the other viability or function assays described previously is the ability of ALAMAR BLUE™ to be used repetitively, day after day, as a non-toxic indicator. This has been shown to be critically important to some cold-stored tissues such as human skin cells.

Hypothermic preservation of cells, tissues and organs is important for the storage of cell lines useful for biomedical research, preservation of forensic samples, storage of medical samples (such as biopsy material and samples for in vitro fertilization, etc.), and for maintenance of cells, tissues and organs for transplantation. For example, the preservation of pancreatic islet cells is critically important to the future of clinical cell transplantation. Korbutt and Pipeleers (6) have shown that rat pancreatic beta cells can survive a 96 h storage period at 4 ° C. in VIASPAN®. Other groups (7) have shown that hepatocyte suspensions can be stored in UW solution. Levi et al. (8) have tested UW solution as a potential cold-storage solution for nerve cells in the consideration of a future nerve bank as a source of material to repair damaged nerves. Gall bladder biliary epithelial cells have also been tested in cold-storage solutions (9). Finally, it has shown that isolated human skin cells growing in culture can be very well preserved in HYPOTHERMO-SOL® (CMS, Rockville, Md.)(10).

Many of these studies tested a variety of additives that enhanced the cold-storage efficacy of hypothermic preservation solutions, but none have done so in view of how cells die following long-term storage in such preservation solutions. A variety of supplements have been added to hypothermic-storage solutions to test their potential as beneficial adjuncts. Rodriguez et al. (7) have shown that the addition of glutathione to UW solution is beneficial to the preservation of hepatocytes. Lopukhin et al. (11) have shown that the addition of 2,3 butanedione monoxime to UW solution increases the storage life of preserved heart. Glycine, however, was found to not be beneficial when added to UW solution (14). Of particular interest, however, is the addition of antioxidants. Lazaroids, for instance, have been shown to increase the cold storage efficacy of UW solution (15,21). Glutathione has been shown to enhance the storage of lung when added to VIASPAN® (19).

Prior studies employing both chill preservation and cryopreservation techniques indicate that a barrier exists for each cell population which precludes full recovery from cold storage. The emergence of engineered tissues utilized in clinical applications, basic research and product safety testing has heightened the demand for improved chill preservation and cryopreservation techniques to ensure the viability of both cells and engineered multi-layered tissues subjected to hyopthermic storage conditions (38).

SUMMARY OF THE INVENTION

The invention relates to cell-free solution compositions for hypothermic storage of animal or human organs, tissues or cells, the cell-free solutions comprising:

(a) one or more electrolytes selected from the group consisting of potassium ions at a concentration ranging from about 35–45 mM, sodium ions ranging from about 80–120 mM, magnesium ions ranging from about 2–10 mM, and calcium ions ranging from about 0.01–0.1 mM;

(b) a macromolecular oncotic agent having a size sufficiently large to limit escape from the circulation system and effective to maintain oncotic pressure equivalent to that of blood plasma and selected from the group consisting of human serum albumin, polysaccharide and colloidal starch;

(c) a biological pH buffer effective under physiological and hypothermic conditions;

(d) a nutritive effective amount of at least one simple sugar;

(e) an impermeant and hydroxyl radical scavenging effective amount of mannitol;

(f) an impermeant anion impermeable to cell membranes and effective to counteract cell swelling during cold exposure, said impermeant ion being at least one member selected from the group consisting of lactobionate, gluconate, citrate and glycerophosphate like compounds;

(g) a substrate effective for the regeneration of ATP, said substrate being at least one member selected from the group consisting of adenosine, fructose, ribose and adenine;

(h) at least one agent which regulates apoptotic cell death;

(i) at least one agent which regulates nitrous oxide synthase activity; and (j) at least one agent which regulates cellular levels of free radicals.

The invention also provides for cell-free solution compositions for hypothermic storage of animal or human organs, tissues or cells between about 5° C. and 0° C., wherein the at least one agent which regulates apoptotic cell death is a member selected from the group consisting of vitamin E and EDTA.

The invention further relates to a cell-free solution composition for hypothermic storage of animal or human organs, tissues or cells between about 5° C. and 0° C., wherein the at least one agent which regulates apoptotic cell death comprises an agent which regulates apoptosis.

The invention further relates to a cell-free solution composition for hypothermic storage of animal or human organs, tissues or cells in cryostorage between a temperature at which the onset of freezing occurs to about −196° C., wherein the at least one agent which regulates apoptotic cell death comprises an agent which regulates apoptosis.

The invention also relates to a cell-free solution composition for hypothermic storage of animal or human organs, tissues or cells, wherein the agent which regulates apoptosis comprises an inhibitor of a caspase protease.

The invention additionally relates to a method of storing of animal or human organs, tissues or cells at a hypothermic temperature comprising:

(a) combining cells with a cell-free solution composition for hypothermic storage having at least one agent which regulates apoptotic cell death and (b) chilling cells to between about 10° C. and 0° C.

The invention also relates to a method of storing animal or human cells at a hypothermic temperature comprising (a) combining cells with a cell-free solution composition for hypothermic storage having at least one agent which regulates apoptotic cell death and (b) chilling cells to between the temperature at which the onset of freezing occurs to −196° C.

By way of definition, agents regulating apoptotic cell death are typically referred to as apoptotic inhibitors. Agents which regulate cellular levels of free radicals are commonly known as free radical scavengers. Agents which regulate nitrous oxide synthase activity are essentially upstream modulators of nitrous oxide production.

Figure 1:
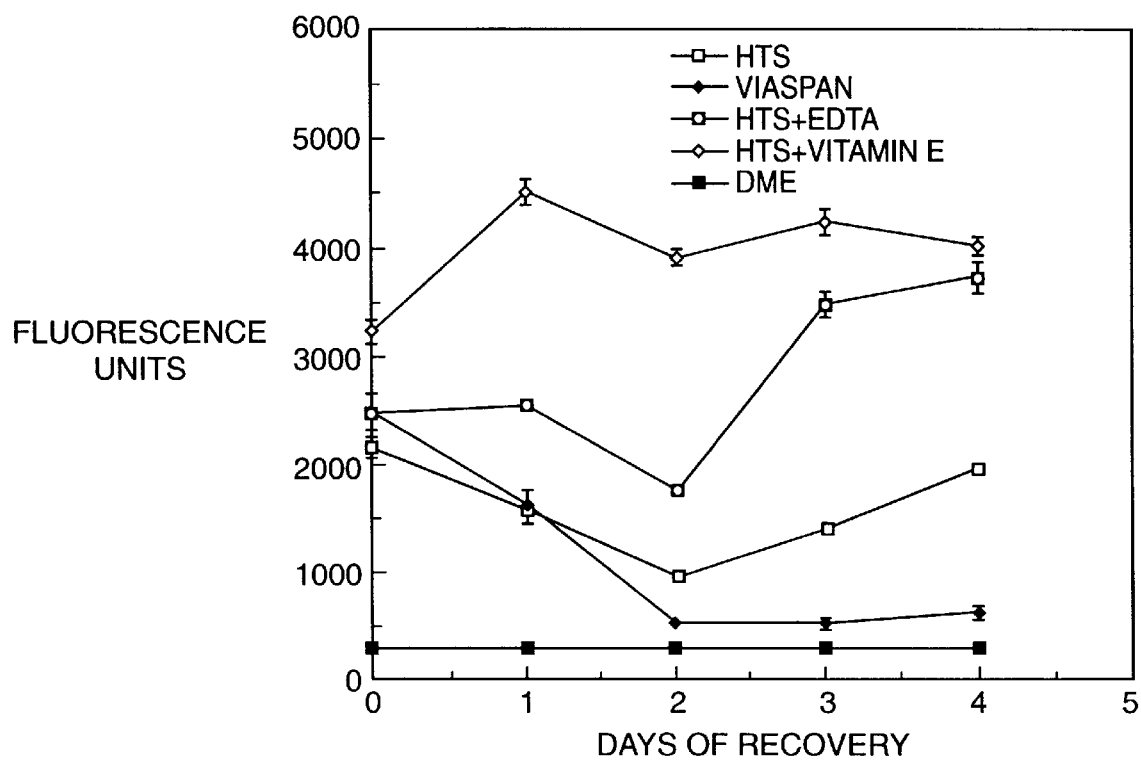
FIG. 1. Effect of 7 days chill preservation of Madin Darby Canine Kidney (MDCK) cells in DME, VIASPAN®, HYPOTHERMOSOL®, HYPOTHERMOSOL® with EDTA or HYPOTHERMOSOL® with Vitamin E. MDCK cells were grown to confluence in 24 well plates and subjected to cold-storage at 4° C. in one of the above 5 solutions. At the end of 7 days cells were moved from 4° C. to 37° C. for an additional 4 days. Cell viability was assayed on each of these days. Note that the efficacy of the chill preservation solutions was HYPOTHERMOSOL® with Vitamin E>HYPOTHERMOSOL® with EDTA>HYPOTHERMOSOL®>VIASPAN®>DME.

C. for various times in either DME or HYPOTHERMO-SOL® as follows: Lane 1—Molecular weight markers; Lane 2—Adherent cells after 1 day cold-storage in DME; Lane 3—Lifted cells after 1 day cold storage in DME; Lane 4—Lifted cells after 2 days cold storage in DME; Lane 5—Adherent cells after 1 day cold storage in HYPOTHERMOSOL®; Lane 6—Lifted cells after 1 day cold storage in HYPOTHERMOSOL®; Lane 7—Lifted cells after 2 days cold storage in HYPOTHERMOSOL®; Lane 8—Lifted cells after 4 days cold storage in HYPOTHERMOSOL®; Lane 9—Lifted cells after 5 days cold storage in HYPOTHERMOSOL®; Lane 10—Lifted cells after 6 days cold storage in HYPOTHERMOSOL®.

Figure 7:
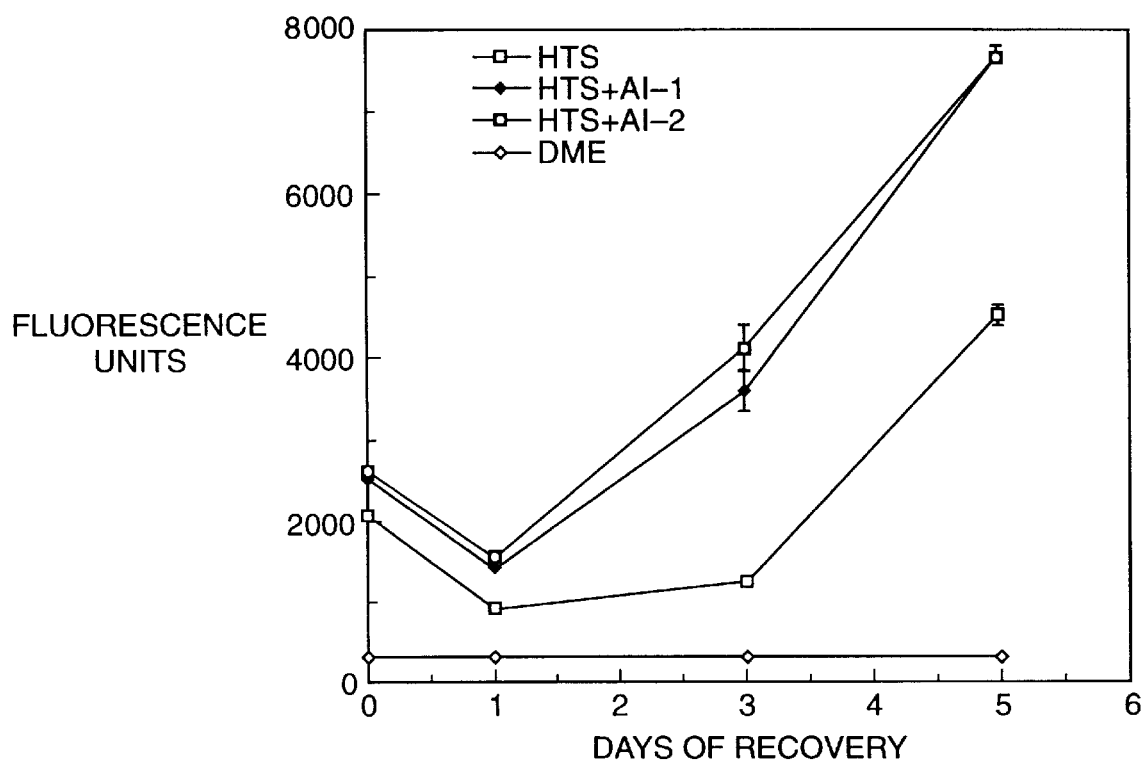

FIG. 7. Effect of 6 days chill preservation of MDCK cells in DME, HYPOTHERMOSOL®, HYPOTHERMOSOL® with IDUN-1529 (HTS+AI-1, 100 μM) and HYPOTHERMOSOL® with IDUN-1965 (HTS+AI-2, 100 μM). MDCK cells were grown to confluence in 24 well plates and subjected to cold-storage at 4° C. in one of the above 4 solutions. At the end of 6 days cells were moved from 4° C. to 37° C. for an additional 5 days. Cell viability was assayed on each of these days. Note that both inhibitors improved the cold-storage capabilities of HYPOTHERMOSOL®.

Figure 8:
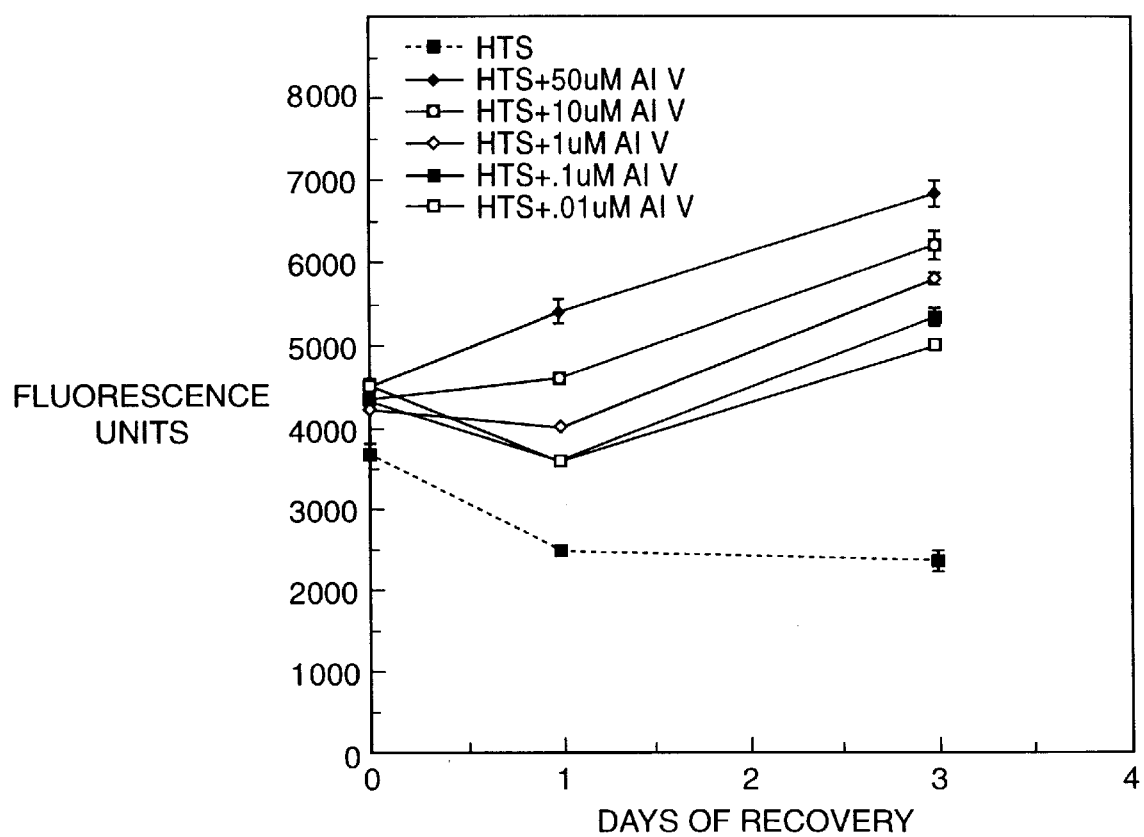

FIG. 8. Effect of 7 days chill preservation of MDCK cells in HYPOTHERMOSOL® and HYPOTHERMOSOL® with indicated concentrations of Caspase-1 Inhibitor V (AI V). MDCK cells were grown to confluence in 24 well plates and subjected to cold-storage in HYPOTHERMOSOL® containing one of the above 5 inhibitor solutions or HYPOTHERMOSOL® containing no inhibitor. At the end of 7 days cells were moved from 4° C. to 37° C. for an additional 3 days. Cell viability was assayed on each of these days. Note that this inhibitor improved the cold-storage capabilities of HYPOTHERMOSOL® in a dose-dependent manner.

Figure 9:
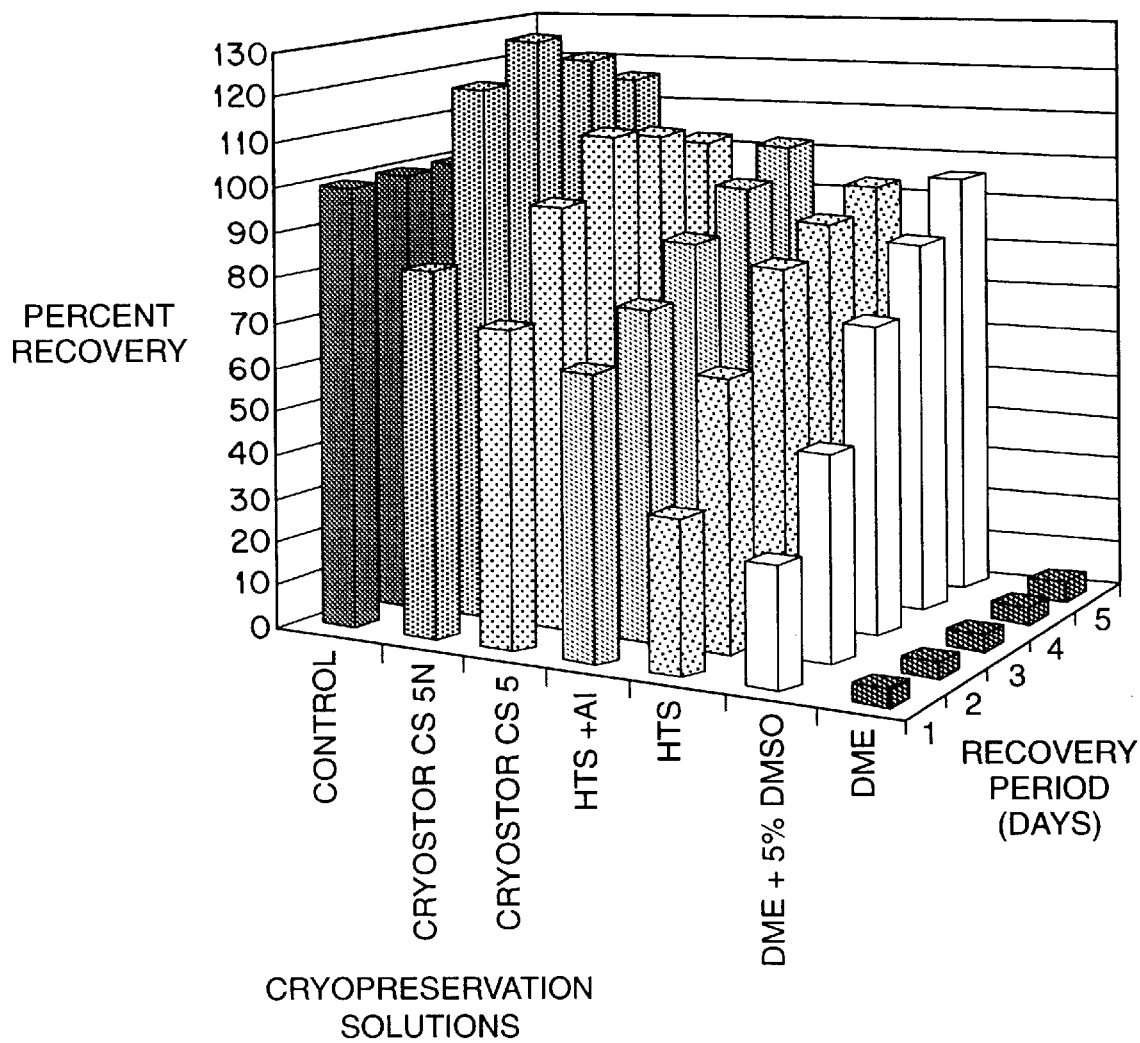

FIG. 9. Five-day post-thaw recovery comparison of MDCK cells cryopreserved in intracellular-like solutions: HYPOTHERMOSOL® (HTS), HTS+apoptosis inhibitor (caspase I inhibitor V), CRYOSTOR CS 5™ and CRYOSTOR CS 5N™ (CRYOSTOR CS 5™+caspase I inhibitor V). Standard deviations and statistical significance are reported in Table I.

Figure 10:
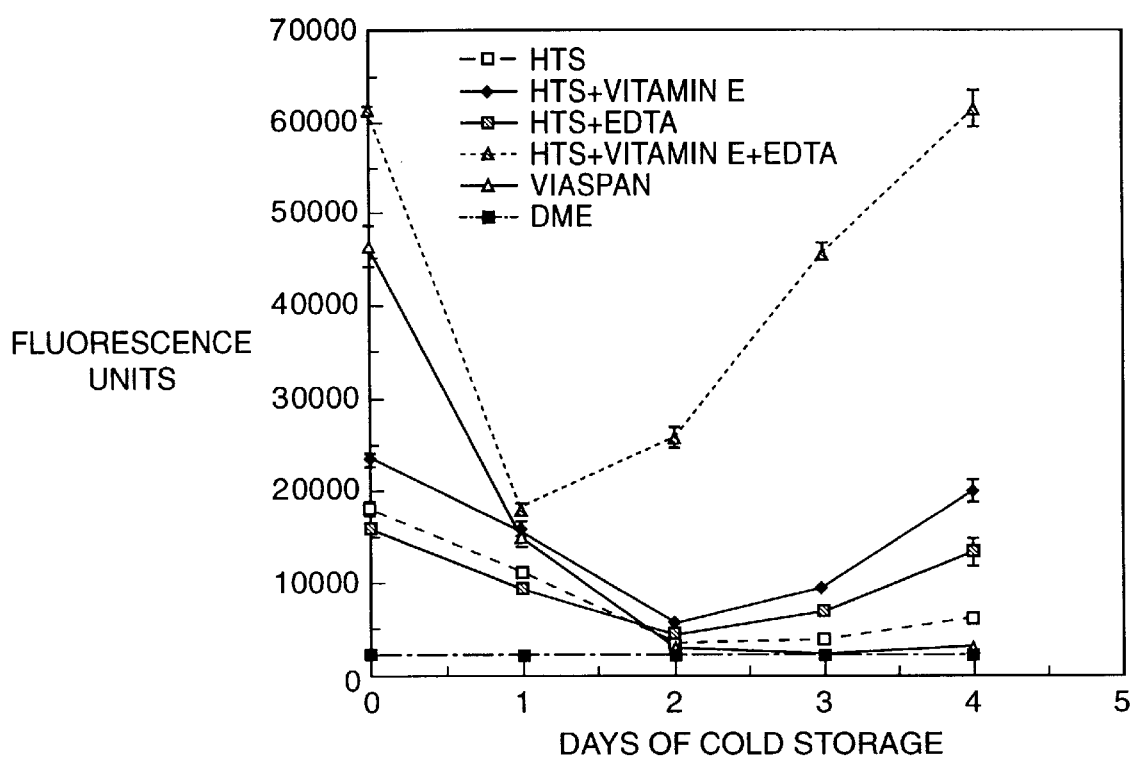

FIG. 10. Effect of 11 days chill preservation of MDCK cells in DME, VIASPAN®, HYPOTHERMOSOL®, HYPOTHERMOSOL®) and Vitamin E, HYPOTHERMOSOL® and EDTA, HYPOTHERMOSOL® with EDTA and Vitamin E. MDCK cells were grown to confluence in 24 well plates, stored for 11 days in the cold at 4° C., and then assayed each day thereafter at 37° C. Note that the order of efficacy is HTS+Vitamin E and EDTA>HTS+Vitamin E>TS+EDTA>HTS>VIASPAN®>DME. The data indicate that the effects of Vitamin E and EDTA might be additive.

Figure 11:
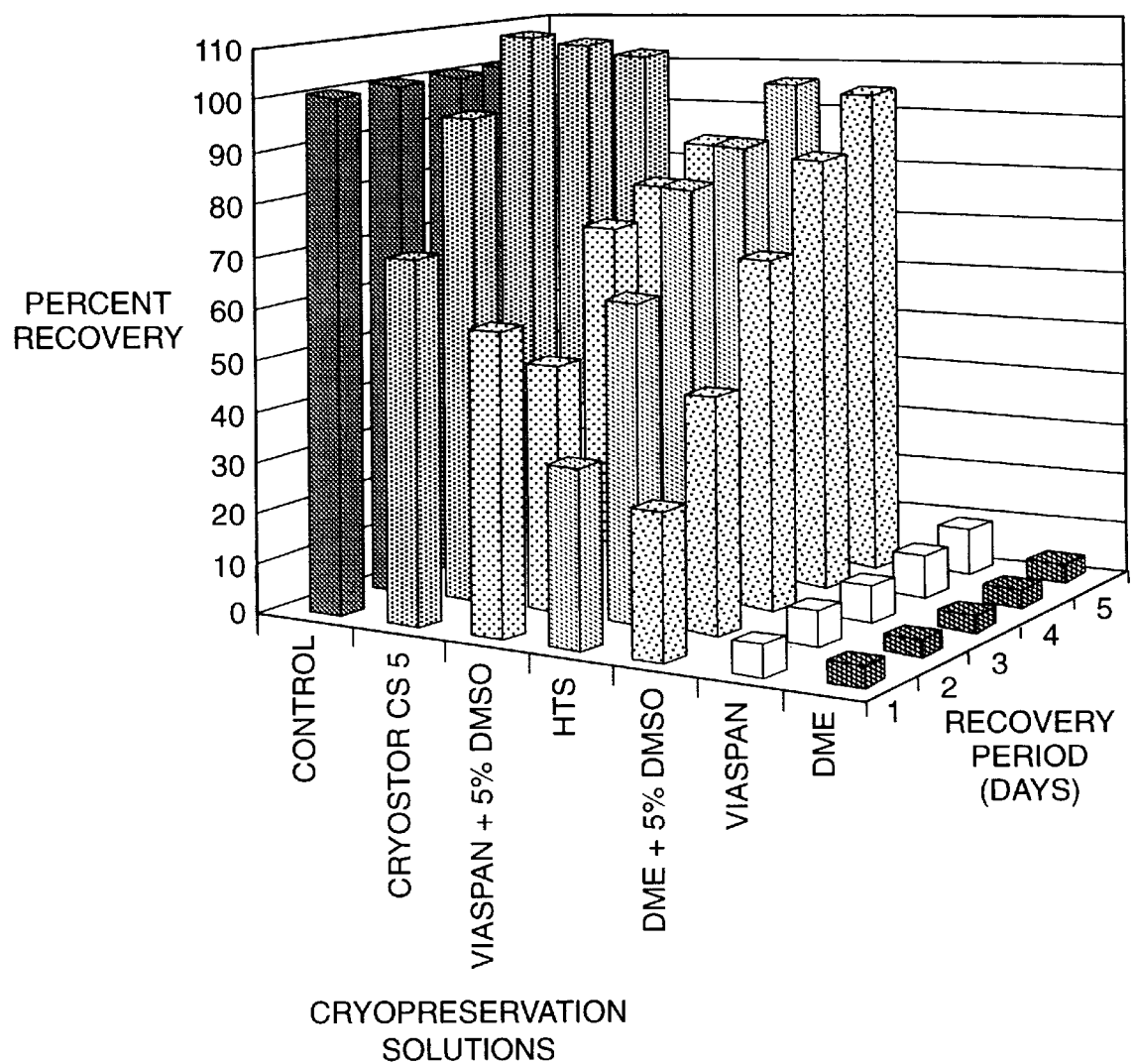

FIG. 11. Comparison of 5-day post-thaw recovery of MDCK cells cryopreserved (−196° C.) in various intracellular-like carrier solutions (HTS and VIASPAN®) with and without cryoprotective agent addition. Standard deviations and statistical significance are reported in Table 1.

Figure 12:
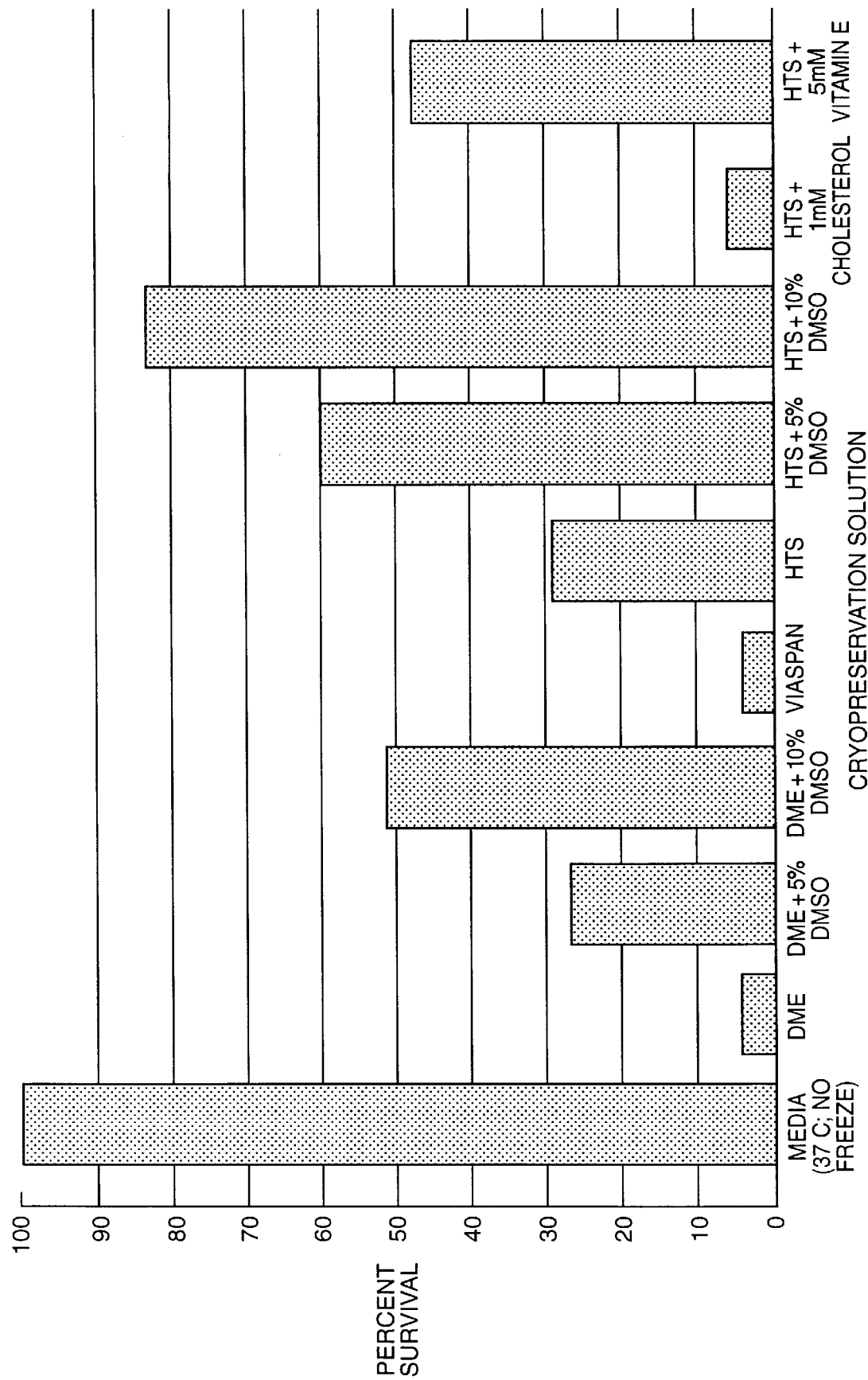

FIG. 12. A sample experiment illustrating the percent survival of the MDCK cell line 24 hours after thawing from 24 hours cryostorage in liquid nitrogen (about −196° C.).

Figure 13:
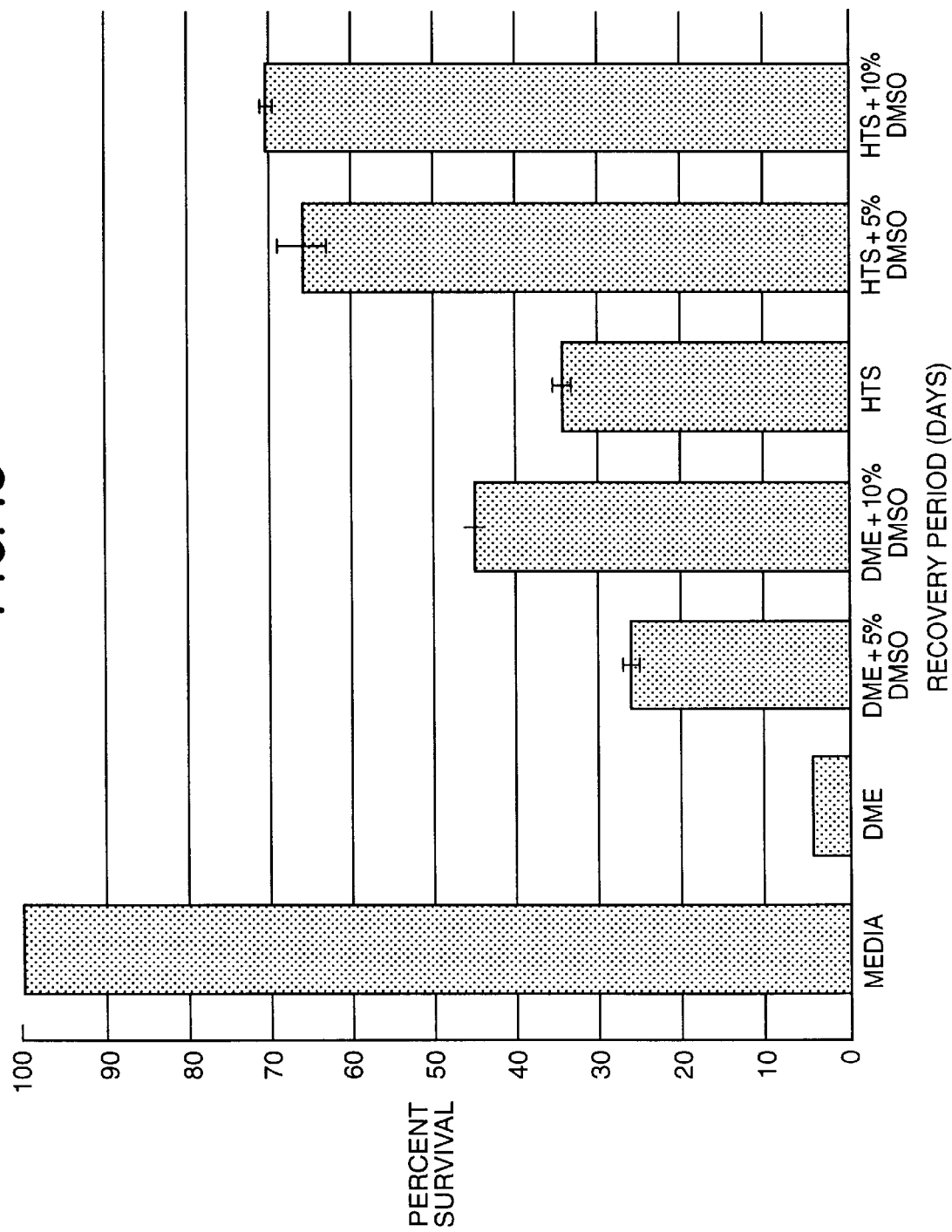

FIG. 13. A comparison between the cryopreservation effects of DME and HTS with and without the indicated levels of DMSO, versus a media, non-frozen control. Legend descriptions are as in FIG. 12.

Figure 14:
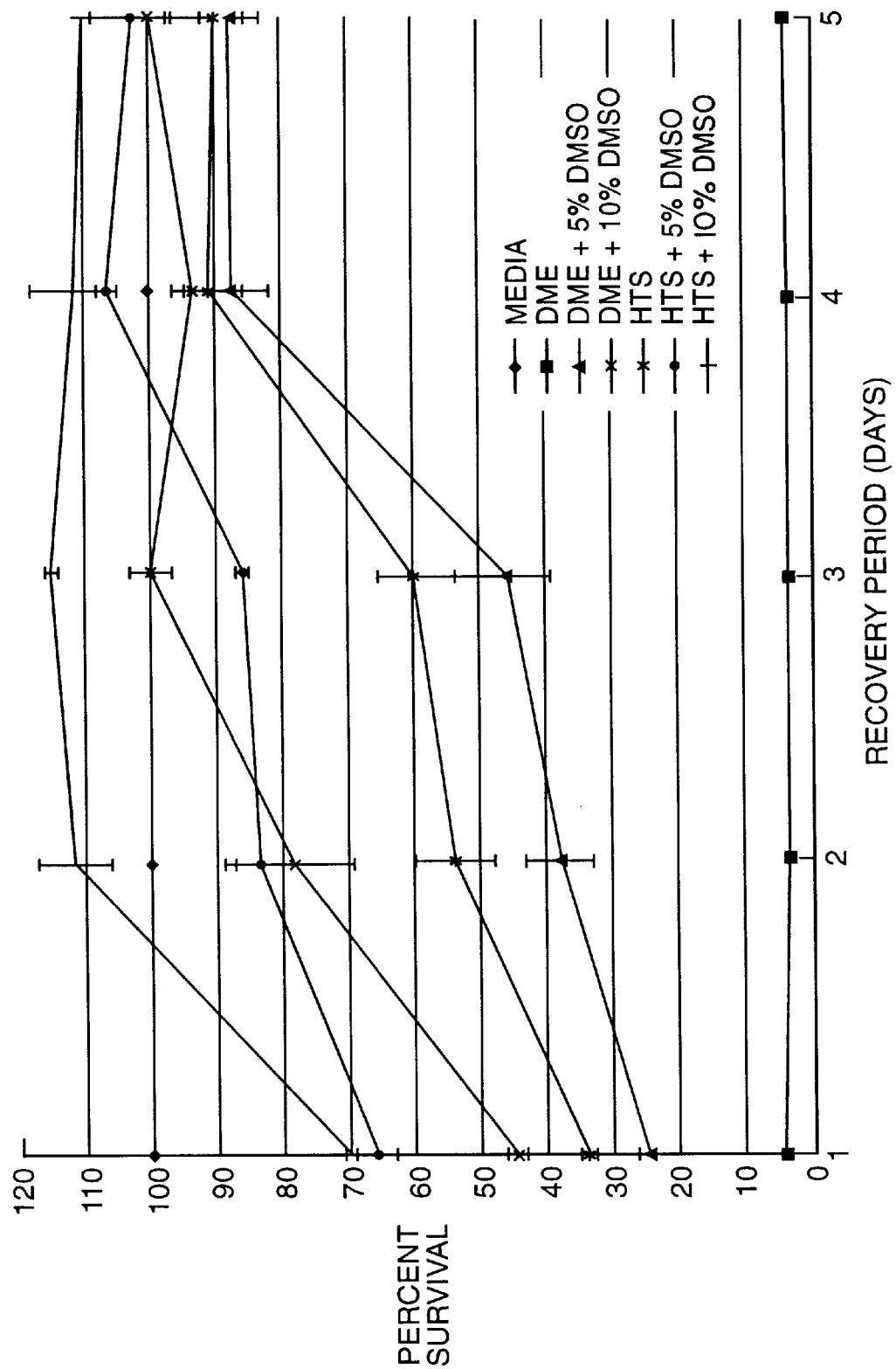

FIG. 14. An illustration of the groups described in FIG. 13, wherein cells were frozen for 1–7 days in liquid nitrogen (duration per group is unimportant) and a post-freeze recovery period of 1–5 days was measured. The inclined slopes indicate cell recovery over time. The recovery process is accelerated when HTS is used as the cryoprotectant media or the carrier media for DMSO.

DETAILED DESCRIPTION OF THE INVENTION

An embodiment invention relates to improvement of cell-free solution compositions for hypothermic storage of animal or human organs, tissues or cells. HYPOTHERMOSOL® is a cell-free solution comprising:

(a) one or more electrolytes selected from the group consisting of potassium ions at a concentration ranging from about 35–45 mM, sodium ions ranging from about 80–120 mM, magnesium ions ranging from about 2–10 mM, and calcium ions ranging from about 0.01–0.1 mM;

(b) a macromolecular oncotic agent having a size sufficiently large to limit escape from the circulation system and effective to maintain oncotic pressure equivalent to that of blood plasma and selected from the group consisting of human serum albumin, polysaccharide and colloidal starch;

(c) a biological pH buffer effective under physiological and hypothermic conditions;

(d) a nutritive effective amount of at least one simple sugar;

(e) an impermeant and hydroxyl radical scavenging effective amount of mannitol;

(f) an impermeant anion impermeable to cell membranes and effective to counteract cell swelling during cold exposure, said impermeant ion being at least one member selected from the group consisting of lactobionate, gluconate, citrate and glycerophosphate;

(g) a substrate effective for the regeneration of ATP, said substrate being at least one member selected from the group consisting of adenosine, fructose, ribose and adenine; and (h) glutathione.

Normal human epidermal keratinocytes (NHEK) stored in HYPOTHERMOSOL® (HTS) or skin culture medium for long periods, for example more than 5 days, can appear quite viable during the first day of recovery comparable to controls that were not cold-stored. However, after 48 hours of recovery, cultured cells may rapidly deteriorate to the point that none of the cells are viable within a few days of recovery (10). A similar dramatic profile occurs with engineered human epidermis (5). MDCK cells stored for long periods at 0° C.–5° C. in VIASPAN®, a commercially available solution designed for hypothermic maintenance of livers and kidneys, also seem to show this time-dependent deterioration (FIG. 1). This time-dependent death may indicate that ATP-dependent gene activity needs to be triggered as a requirement for cell death.

As a cryoprotective solution, HTS is comparable to that of cell culture media containing DMSO (FIGS. 3, 9, 11, 13, 14). VIASPAN® fails as a cryopreservation media, but upon supplementation with DMSO provides limited improved cell survival over that of cell culture media with DMSO (FIG. 11). An HTS derivative containing 5% DMSO (CRYOSTOR™ CS 5), is a superior cryopreservation solution compared to either cell culture media or VIASPAN® fortified with DMSO (FIG. 11).

Figure 2:
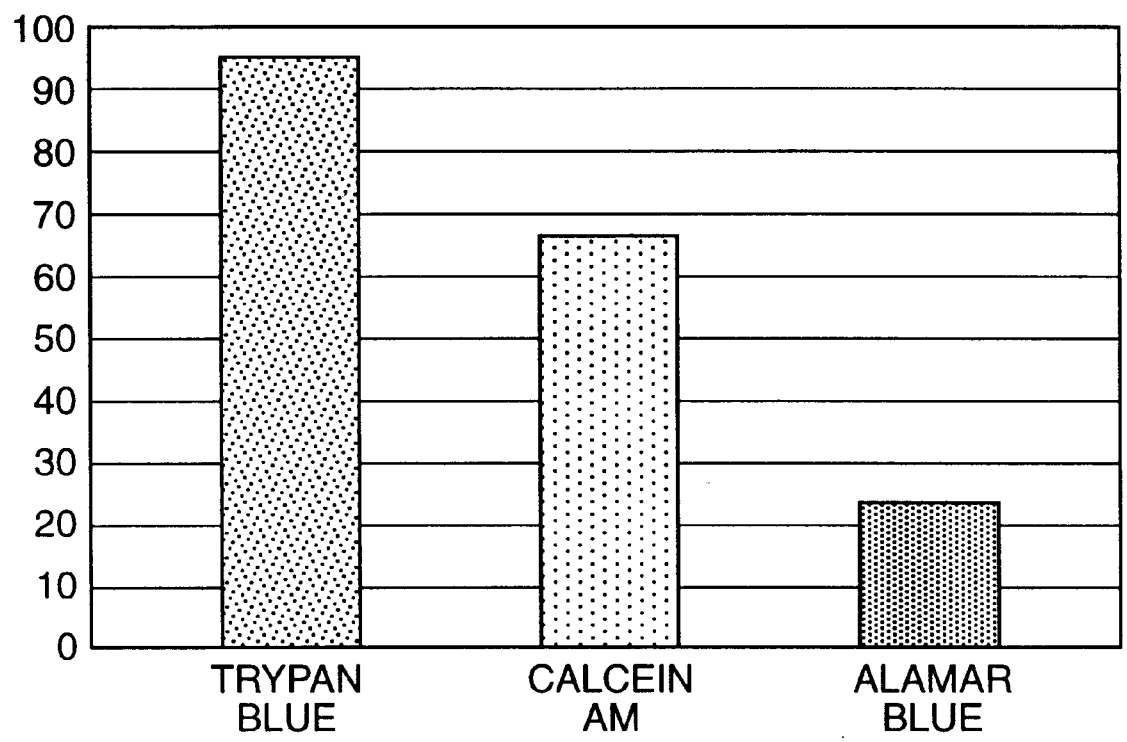
FIG. 2. Comparison of percent survival outcome of cryopreserved (−196° C.) MDCK cells utilizing various assessment assays.

Traditionally, cryopreservation success has been assessed within a few hours of thawing using dye exclusion assays. However, numerous reports state that dye exclusion assays tend to overestimate cell survival (33). The identification of an assessment assay that would yield a more accurate representation of the cellular survival following cryopreservation over an extended time period was explored. Comparisons between trypan blue exclusion, Calcein-AM, and ALAMAR BLUE™ were performed to assess post-thaw viability of cryopreserved MDCK cells stored in DME+5% DMSO. The resulting percent survival levels from the trypan blue, Calcein-AM, and ALAMAR BLUE™ assays were 95%, 65%, and 28%, respectively (FIG. 2). Based upon these observations, ALAMAR BLUE™, the more stringent assay, was selected as the primary assessment probe. The ALAMAR BLUE™ assay is a non-toxic, physiological indicator dye that measures metabolic activity based upon the terminal oxidative step in aerobic respiration (48). Also, since ALAMAR BLUE™ is a multi-end point assay, monitoring long-term cell survival and recovery was possible.

Figure 3:
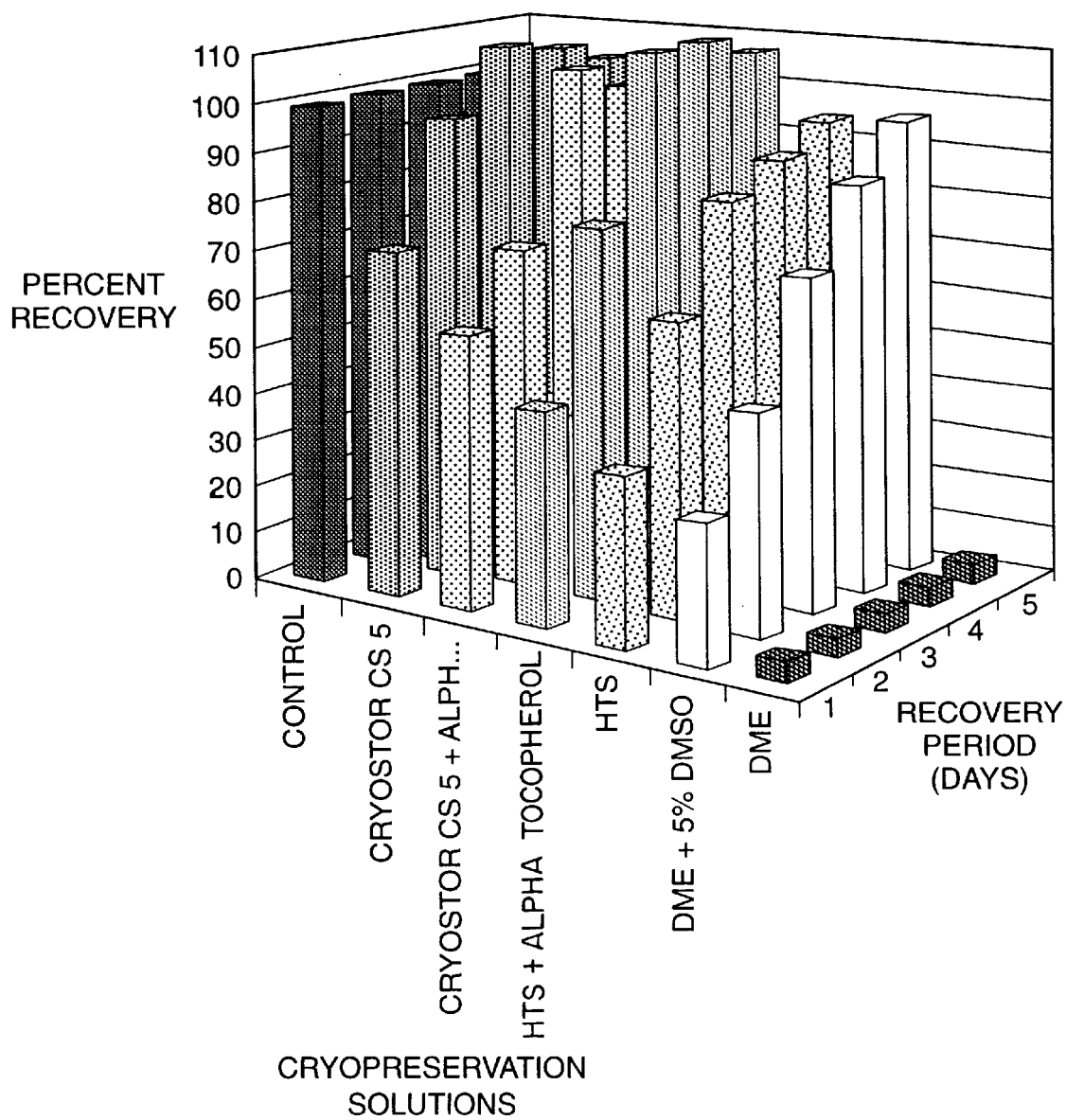
FIG. 3. Five-day post-thaw recovery comparison outcome of MDCK cells cryopreserved (−196° C.) in both extracellular-like (DME) and intracellular-like (HTS) carrier solutions with and without cryoprotective agent addition. Standard deviations and statistical significance is reported in Table 1. Note: CRYOSTORE CS5® is HTS+5%DMSO.

An object of the invention is enhancement of cryopreservation through the alteration of the carrier media, extracellular-type (DME) vs. intracellular-type (HTS). Cells were cryopreserved in DME+5% DMSO and compared to cells preserved in HTS+5% DMSO (CRYOSTOR™) (FIG. 3). Cells cryopreserved in CRYOSTOR™ CS5 (HTS+5% DMSO) yielded a 257% increase in survival compared to cells cryopreserved in DME+5% DMSO, as well as recovering to 100% in approximately half the time. This significant increase in survival and rate of recovery ($P<0.007$) appeared to be a result of the carrier media difference. To test this hypothesis cell cultures were also cryopreserved in base HTS (DMSO free). Comparing DME+5% DMSO and HTS, post-thaw survival equaled 28% and 32% ($P=0.145$), respectively (FIG. 3). The long-term recovery of cells cryopreserved in HTS mirrored that of DME+5% DMSO recovering to 95% of controls within 5 days. Thus, the chill preservation solution HTS functioned well as a cryopreservation medium without additional cyroprotectant agent supplementation.

Despite the improvement in cryopreservation survival through the use of an intracellular-like solution (HTS), the overall outcome still yielded a significant percent failure of survival (28%) (FIG. 3). This level of preservation failure is routinely encountered even with optimized cryopreservation protocols. In view of this common problem, the inventors suggested that one or more modes of cell death beyond those addressed by traditional chemo-osmotic protective strategies might be responsible for some or all of the cell death. Osmotic-based protection might be limited ("capped") due to the possible failure of standard cryoprotectants to inhibit programmed cell death (apoptosis).

TABLE 1

| | | DME (4.2%) | DME + 5% DMSO (27.6%) | HTS (34.6%) | HTS + α-tocopherol (43.8%) | HTS + caspase I inhibitor V (64.6%) | CryoStor CS 5 (72.3%) | CryoStor CS 5 + α-tocopherol (56.4%) | CryoStor CS 5N (84.1%) | Viaspan (5.1%) | Viaspan + 5% DMSO (58.3%) | Control (37° C.) (100%) |
|---|---|---|---|---|---|---|---|---|---|---|---|---|
| | | | | | | | 1 Day | | | | | |
| DME (3.7%) | | N > 150 SD ± 0.65% | P < 0.0001 | P < 0.0001 | P < 0.0001 | P < 0.0001 | P < 0.0001 | P < 0.0001 | P < 0.0001 | P = 0.7822 | P < 0.0001 | P < 0.0001 |
| DME + 5% DMSO (69.3%) | | P = 0.0003 | N > 150 SD ± 2.3% | P = 0.0027 | P = 0.0001 | P = 0.0014 | P < 0.0001 | P < 0.0001 | P < 0.0001 | P < 0.0001 | P < 0.0001 | P < 0.0001 |
| HTS (81.6%) | | P < 0.0001 | P = 0.0266 | N > 150 SD ± 4.5% | P = 0.0004 | P = 0.0052 | P < 0.0001 | P < 0.0001 | P < 0.0001 | P < 0.0001 | P < 0.0001 | P < 0.0001 |
| HTS + α-tocopherol (114.3%) | | P < 0.0001 | P = 0.0001 | P = 0.0017 | N > 50 SD ± 2.3% | P = 0.0798 | P < 0.0001 | P = 0.3227 | P < 0.0001 | P < 0.0001 | P = 0.3675 | P < 0.0001 |
| HTS + casapse I inhibitor V (85.8%) | | P < 0.0001 | P = 0.0049 | P = 0.6504 | P < 0.0001 | N > 50 SD ± 5.8% | P = 0.0102 | P < 0.0001 | P = 0.0006 | P < 0.0001 | P < 0.0001 | P < 0.0001 |
| CryoStor CS 5 (109.2%) | | P < 0.0001 | P = 0.0003 | P = 0.0083 | P = 0.3239 | P = 0.0012 | N > 150 SD ± 7.2% | P = 0.0002 | P = 0.0001 | P < 0.0001 | P < 0.0001 | P < 0.0001 |
| CryoStor CS 5 + α-tocopherol (104.8%) | | P < 0.0001 | P = 0.0003 | P = 0.0219 | P = 0.0244 | P = 0.0035 | P = 0.2723 | N > 50 SD ± 5.6% | P < 0.0001 | P < 0.0001 | P = 0.6247 | P < 0.0001 |
| CryoStor CS 5N (133.7%) | | P < 0.0001 | P < 0.0001 | P < 0.0001 | P < 0.0001 | P < 0.0001 | P = 0.0004 | P = 0.0001 | N > 50 SD ± 4.6% | P < 0.0001 | P < 0.0001 | P < 0.0001 |
| Viaspan (6.9%) | | P = 0.4933 | P < 0.0001 | P < 0.0001 | P < 0.0001 | P < 0.0001 | P < 0.0001 | P < 0.0001 | P < 0.0001 | N > 50 SD ± 0.65% | P < 0.0001 | P < 0.0001 |
| Viaspan + 5% DMSO (73.2%) | | P < 0.0001 | P = 0.0651 | P = 0.1222 | P < 0.0001 | P = 0.0005 | P < 0.0001 | P = 0.0001 | P < 0.0001 | P < 0.0001 | N > 50 SD ± 8.57% | P < 0.0001 |
| Control (37° C.) (100%) | | P < 0.0001 | P = 0.0006 | P = 0.0396 | P < 0.0001 | P = 0.0003 | P = 0.0228 | P = 0.1604 | P < 0.0001 | P < 0.0001 | P < 0.0001 | N > 150 SD ± 8.38% |
| | | | | | | | 3 Days | | | | | |

Post-thaw recovery periods (1 & 3 days) of cryopreserved MDCK cells.
Diagonal squares (highlighted) illustrate sample size and standard deviation for day 1 recovery values.
Values in table legends represent percent recovery of MDCK cells at day 1 and day 3.
All other values represent confidence limits (P-values) determined by ANOVA.

Accordingly, an object of the invention is to reduce cryopreservation failure by impairing the modes of cell death associated with cryopreservation failure. One approach is a free-radical protective strategy, in which protective factors are included in hypothermic cell preservation solutions to enhance post-thaw cell survival. α-Tocopherol (Vitamin E) addition to HTS yielded a 162% survival advantage over that of cells cryopreserved in base HTS. α-Tocopherol plus HTS afforded a 185% survival advantage over DME+5% DMSO, with a recovery rate equivalent to that of HTS+5% DMSO (CRYOSTOR™ CS 5) (FIG. 3). Interestingly, this antioxidant did not provide additional long-term benefit and was actually detrimental when used in conjunction with HTS+5% DMSO (FIG. 3). The addition of α-tocopherol to CRYOSTOR™ CS 5 (HTS+5% DMSO) yielded a survival rate of 56%, which is significantly lower than the overall 72% survival of cells preserved CRYOSTOR™ CS 5 (HTS+5% DMSO) alone. This observation further supports the idea that cell death outside the "cryopreservation cap" may be due to one or more other factor(s) not related to extracellular ice formation and resulting chemo-osmotic perturbations.

Figure 4:
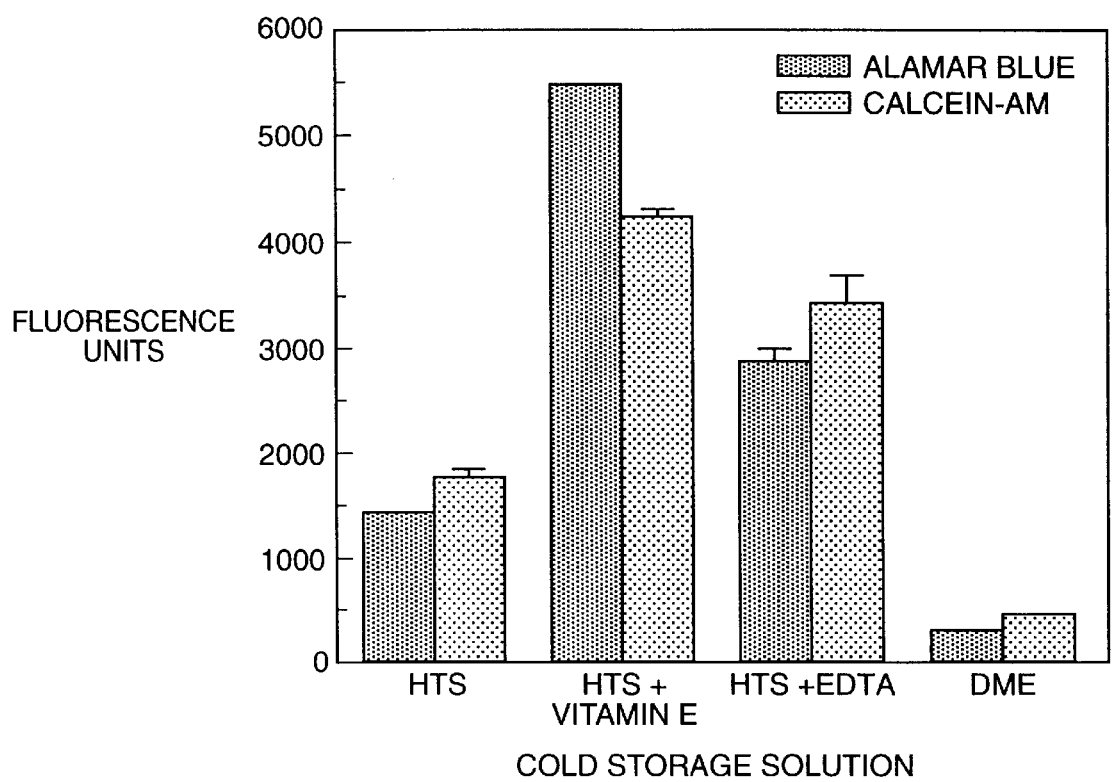
FIG. 4. Effect of 7 days chill preservation of MDCK cells in DME, HYPOTHERMOSOL®, HYPOTHERMOSOL® with EDTA or HYPOTHERMOSOL® with Vitamin E-cell membrane integrity and viability assays. MDCK cells were grown to confluence in 24 well plates and subjected to cold-storage for 7 days at 4° C. in DME, HYPOTHERMOSOL®, HYPOTHERMOSOL® with Vitamin E or HYPOTHERMOSOL® with EDTA. Cells were assayed immediately after removal from the cold with ALAMAR BLUE™ and Calcein-AM. Note that the fluorescence levels were highest in cells stored in HYPOTHERMOSOL® supplemented with Vitamin E indicating that this solution is best able to preserve viability (ALAMAR BLUE™) and plasma membrane integrity (Calcein-AM).

In addition, both α-tocopherol (Vitamin E) and EDTA increase the efficacy of HYPOTHERMOSOL® as a chill preservation agent. FIG. 4 shows the addition of EDTA to HYPOTHERMOSOL® enhanced the chill preservation capability of the solution at 0° C. to 5° C., as evidenced by both ALAMAR BLUE™, a metabolic dye, and Calcein, a membrane integrity dye. Both agents could be working in a variety of manners. EDTA may act as chelator of extracellular calcium ions, which are known to be cytotoxic at high intracellular concentrations. EDTA could thus dampen the effects of calcium-activated proteases and/or calcium-activated endonucleases. The beneficial effect of Vitamin E might be due to its antioxidant ability, thereby possibly preventing membrane damage during hypothermic cell storage. Alternatively, Vitamin E might be inhibiting the release of nitric oxide (22). Since Vitamin E has been reported to protect cells from apoptosis (23), experiments were performed to determine if cells die through necrosis or programmed cell death, (apoptosis), when stored for lengthy periods in HYPOTHERMOSOL®.

Cell death can occur through apoptosis or necrosis (for a review see 24), in response to a variety of stresses (28). A 1998 report by Hollister et al. (36) demonstrated that apoptosis is initiated following freezing exposure (−5° C. to −75° C.) in a non-cryopreservation based study. In addition, Mathew et al. (personal communication) demonstrated that hypothermia also induces apoptosis. Since controlled rate freezing of cryopreserved cells induces numerous stresses, apoptotic cell death is a likely contributor to cryopreservation failure.

Necrosis or pathological cell death is characterized by the loss of cell membrane integrity resulting in cell swelling and is caused by a number of pathological agents. DNA in cells that undergo necrosis is cleaved in a random fashion. Thus, the DNA from cells that have undergone necrosis appears as a continuous smear on an electrophoresis gel. Apoptosis, or programmed cell death, is gene activated and is characterized by shrinking cells, intact plasma membranes, and apoptotic body formation. DNA in cells that undergo apoptosis is cleaved in a non-random fashion, forming upon electrophoresis, a DNA ladder appearing to represent the 200 bp periodicity of the DNA fragments.

Figure 5:
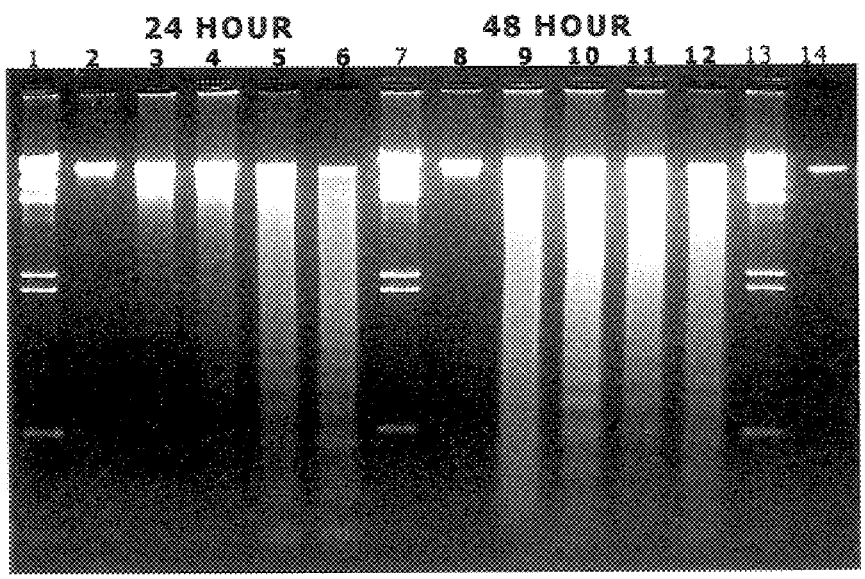
FIG. 5. DNA gel electrophoresis of cryopreserved (−196° C.) MDCK cells 24 and 48 hours post-thaw. Lanes 1, 7 and 13 contain λ DNA cut with HindIII (23.1, 9.4, 6.5, 4.3, 2.3, 2.0 and 0.5 Kb), while lanes 2, 8 and 14 contain intact genomic DNA from isolated living adherent MDCK cells. Lanes 3–6 and 9–12 represent DNA isolated from dead, lifted cells. Lanes 3 and 9 contain DNA from cells preserved in DME, lanes 4 and 10 contain DNA from cells preserved in DME+5% DMSO; lanes 5 and 11 contain DNA from cells preserved in HYPOTHERMOSOL®; and lanes 6 and 12 contain DNA from cells preserved in CRYOSTOR CS 5™.

Cryopreserved cells, both lifted and adherent to cell plates, were collected after recovery periods of 24 and 48-hours for analysis by DNA gel electrophoresis. Upon examination of the DNA gel, several observations concerning cryopreservation failure were noted (FIG. 5). First, in all cryopreservation solution variations, the DNA isolated from living (adherent) cells resulted in a single band at the top of the gel, an indicator of viable cells (FIG. 5). The DNA from the lifted (dead) cells cryopreserved in DME alone revealed a distinct random cleavage pattern (a "smear"). This pattern, which is indicative of necrotic cell death, was especially apparent 48-hours post-thaw. DNA from the lifted cells cryopreserved in DME+5% DMSO revealed 24-hours post-thaw that the preliminary stages of necrosis were occurring, whereas after 48-hours post-thaw, necrotic cell death remained predominant but the appearance of a DNA ladder was observed. This DNA ladder represents 180 base pair DNA fragment derivatives, a hallmark of the final stage of apoptosis. Examination of the lanes containing DNA isolated from lifted cells from HTS and CRYOSTOR™ CS 5 (HTS+5% DMSO) (24 and 48-hour post-thaw) revealed a decreasing pattern of necrotic cell death and an increase in the presence of apoptotic cell death. From DNA analysis it was concluded that apoptosis contributed significantly to cryopreservation failure. Further experimentation is required to determine the relative levels of contribution of necrosis and apoptosis to cryopreservation failure.

Figure 6:
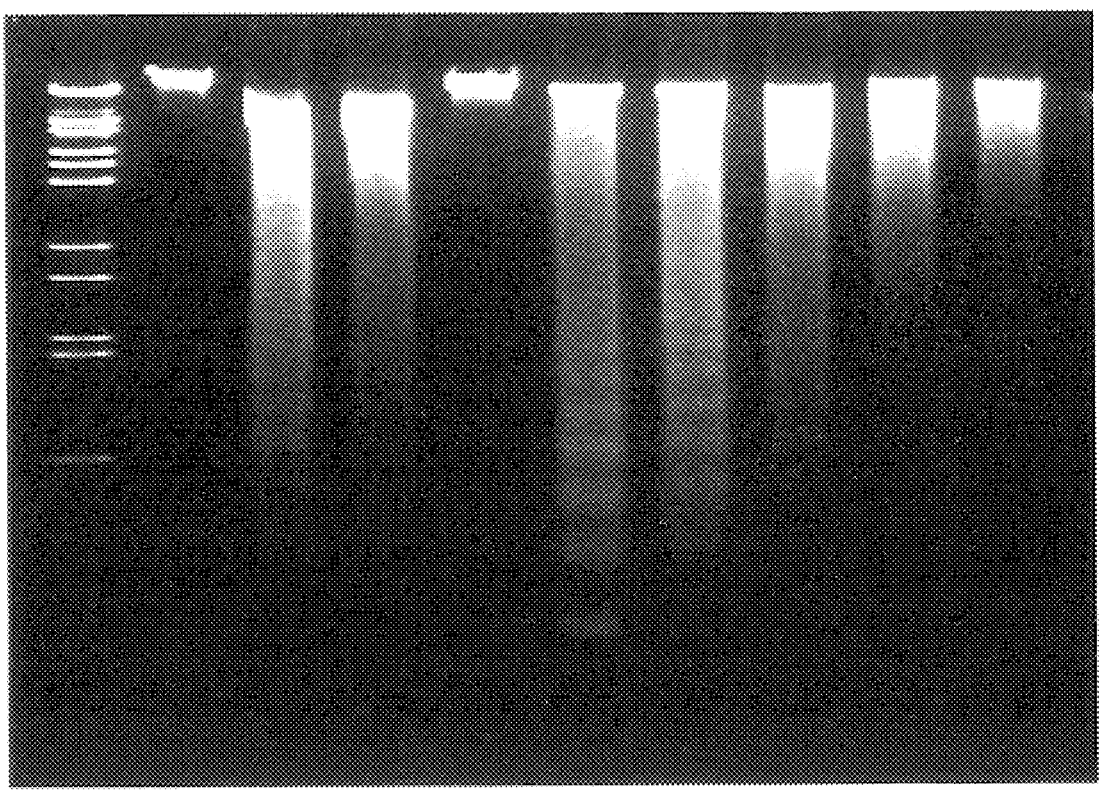
FIG. 6. Gel electrophoresis of DNA isolated from MDCK cells that have undergone chill preservation in DME or HYPOTHERMOSOL®. MDCK cells were cold-stored at 4°

Further examination comparing the DNA of dead, detached, MDCK cells subjected to chill preservation at 4° C. compared to the DNA of living, attached, cells is shown in FIG. 6. The DNA of the dead cells exhibited the characteristic DNA ladder characteristic of apoptotic cells (FIG. 6). This ladder was present in cells cold-stored in either DME (FIG. 6, lanes 3,4) or HYPOTHERMOSOL® (FIG. 6, lanes 6–10). It is important to note, however, that cells stored for longer times in the cold (lanes 9 and 10) appeared to have more necrotic characteristics (i.e. more extensive smear) and fewer apoptotic characteristics (i.e. laddering is less evident). Thus, the data may suggest that chill preserved cells undergo both apoptosis and necrosis, and the transition between both states depends on the cold-storage time.

Additional experiments with apoptosis inhibitors (FIGS. 7 and 8) support the notion that apoptosis may be playing a role in cell death during cold-storage. The IDUN apoptosis inhibitors and Caspase-1 Inhibitor V, both interleukin-1β-converting enzyme (ICE)-like protease inhibitors, protected cells during chill preservation at 4° C. One apparent enigma in the data relates to the level of effectiveness of the apoptosis inhibitors. Note that the principal mode of cell death for cells stored for longer than 5 days in HYPOTHERMOSOL® is necrosis, not apoptosis (FIG. 6, lanes 8 and 9). Yet the apoptosis inhibitors seem quite effective at preventing cell death at these times (FIGS. 7 and 8). One possible interpretation of these data is that the cells that die through necrosis may proceed through an apoptotic sequence first to enter the necrosis pathway. Hirsch et al. (25) have shown that mitochondrial alterations such as permeability transition may be critical in a decision point about cells entering necrosis or apoptosis. More specifically, this group has proposed that the availability of apoptogenic proteases might determine if a cell enters necrosis or apoptosis. Thus, the unpredictable level of effectiveness of apoptosis inhibitors on cells that appear to be going exclusively through necrosis clearly demands future investigation.

In view of the above, an object of the invention is the reduction of apoptotic cell death during cryopreservation by the addition of an apoptotic regulator to HTS. Since the caspase cascade is a part of the endonuclease-based DNA fragmentation process (47), disruption of the caspase cascade was found to reduce the level of apoptosis, thereby improving cryopreservation outcome. As seen in FIG. 9, the addition of the protease inhibitor caspase I inhibitor V to HTS afforded additional protection over that of the base HTS (65% vs. 32% viability, respectively). When cells were cryopreserved in HTS+5% DMSO plus inhibitor (CRYOSTOR CS 5N®), an increase in 24-hour post-thaw survival occurred in comparison with HTS+5% DMSO, and a very significant increase in the outcome compared to standard DME+5% DMSO (85%: 72% 28%, respectively). The use of the inhibitor in HTS+5% DMSO improved the overall cryopreservation outcome to 85% vs. non-cryopreserved control cells. Addition of the inhibitor to HTS with and without DMSO resulted in a more rapid rate of recovery of the cells as well.

The mechanism by which cryopreservation induces apoptosis is unclear, although it is apparent that the activation of the apoptotic mechanism within the cells is a direct result of stress experienced during the freeze-thaw process. One possible explanation might be the physical pressure that is exerted on a cell membrane as a consequence of the "shrinkage and swelling" of a cell during the freeze-thaw process. This structural excursion in combination with profound hyperosmolality may be activating death receptors (35) on a cell's surface resulting in the onset of apoptosis. The improvement in cryopreservation outcome through the incorporation of an apoptotic inhibitor (FIG. 9) suggests that the activation of the caspase cascade occurs during the cryopreservation freeze-thaw process. Another possible means of apoptotic activation might be as a result of free-radical accumulation in the cytosol causing the activation of the mitochondrial permeability transition pore (MPTp). The activation of the MPTp allows for the free diffusion of ions into and out of mitochondria disrupting normal activity therefore resulting in the activation of the caspase cascade (35). Support for this possible avenue of apoptosis initiation was demonstrated by the improvement of cryopreservation outcome with the inclusion of α-tocopherol, a free-radical scavenger, in HTS (FIG. 3). Finally, in response to sub-lethal cellular and DNA damage, the p53 gene may be activated thereby evoking the initiation of the apoptotic mechanism within the cell (31). Cryopreservation-induced apoptosis may not be linked directly to one particular apoptotic induction pathway, but may be due to a combination of apoptotic initiation factors and pathways which contribute to cryopreservation failure. Further studies are necessary to determine which pathways are intimately linked to cryopreservation-induced apoptosis.

A question that remains is whether Vitamin E and/or EDTA exert their protective effects through inhibition of apoptosis. At the current time, this question is not easily answered. Chill preservation of MDCK cells for 11 days at 4° C. in HTS and EDTA plus Vitamin E provided for greater cell viability than HTS supplemented with either EDTA or Vitamin E alone (FIG. 10). Similar experiments testing EDTA and Vitamin E as additives in HTS have been accomplished with chick cardiomyocytes. The data with these excitable cells also show the same protective rank order of additives relative to VIASPAN®. Additional experiments with the water soluble form of Vitamin E, Trolox, showed data identical to those of Vitamin E (data not shown). Thus, whatever the mechanism, Vitamin E and EDTA increase the efficacy of HYPOTHERMOSOL® and the effects of the two agents appear to be additive. These data suggest that the future improvement of hypothermic storage solutions for cells, mammalian organs and engineered tissues should focus on the molecular changes that occur in both the cytoplasm and the genome during cold storage.

The use of a specific intracellular-type solution, HYPOTHERMOSOL®, as both a cryopreservation solution as well as a carrier solution for DMSO during cryopreservation significantly increases post-thaw cell survival. The use of HYPOTHERMOSOL® is thought to reduce the ionic-dependent stresses the cell is exposed to during the freeze-thaw process. In addition, the cell death observed after cryopreservation is not strictly limited to physical freeze-thaw related damage and subsequent freeze-induced traumatic necrosis. For the first time, it is shown that apoptosis is associated with cryopreservation failure. The use of apoptotic inhibitors during cryopreservation according to the invention results in an increase in cryopreservation success. Further, the addition of α-tocopherol, an agent which improves the performance of HTS as a chill preservation solution also improves the cryopreservation capability of HTS. Lastly, the greatest improvement in cryopreservation outcome is achieved by the combined use of CRYOSTOR™ CS 5 (HTS+5% DMSO) and caspase inhibitors that disrupt the apoptotic cascade (CRYOSTOR™ CS 5N). Thus, an inventive HYPOTHERMOSOL® formulation, CRYOSTOR™ CS 5N, is the first preservation solution formulated by design to disrupt the onset of apoptosis induced by cryopreservation.

Additionally, since HTS (DMSO-free) can be used as a cryoprotectant, the preservation solution may be especially useful for clinical tissue engineering applications through the elimination of the multi-step wash procedures currently required by some protocols to remove the DMSO before application. Finally, future exploration into resolving the molecular and/ or physical basis of cryopreservation failure is necessary in order to overcome the limiting "cryopreservation cap."

The invention is envisioned for use in preserving various organs, tissues and cells by both chill preservation at 0° C.–5° C. and by cryopreservation. Organs, including but not limited to lung, liver, heart, kidney, gut, eye and skin may be chill preserved according to the invention prior to transplantation in a recipient patient. Tissues such as bone marrow and cells such as erythrocytes, leukocytes may be cryopreserved for long term storage according to the invention. For example, tissues for forensic and pathology records may be cryostored without significant loss of viability. Cell lines for therapeutic and research interests may be preserved for short or long periods, applying the invention. Of particular interest is long term cryopreservation of gametes and embryos for reproductive procedures such as in vitro fertilization. Variations of the invention may be applied for long term preservation of entire multicellular organisms. In addition to preservation, this method of controlling apoptosis serves to rescue cells and tissues cryopreserved by older methods comprising storage at liquid nitrogen temperatures.

The invention will be further illustrated by means of the following non-limiting examples.

EXAMPLES

Methods

MDCK cell culture. Madin Darby Canine Kidney (MDCK) cells were obtained from the American Type Culture Collection (Rockville, Md.). Stock cultures were maintained at 37° C./95% air/5% $CO_2$ in Falcon T flasks and grown in Dulbecco's modified Eagle's (DME) medium (4500 mg glucose/liter) with 10% fetal bovine serum and 1% penicillin/1% streptomycin (GIBCO-BRL Laboratories, Grand Island, N.Y.). Cells were seeded at a density of approximately 1×10⁵/cm² in Falcon 24 well plates. All cells were confluent when used for hypothermic experiments.

Cold storage and fluorescence assays. The cell culture medium was removed from the MDCK cultures, the cells were washed with Hanks Balanced Salt Solution, and this medium was replaced with either cell culture medium, HYPOTHERMOSOL®, HYPOTHERMOSOL® modified with Vitamin E or EDTA, HYPOTHERMOSOL® modified with apoptosis protease inhibitors, or VIASPAN™, that were each prewarmed to room temperature. The hypothermic media did not contain fetal calf serum. The plates were then placed at 4° C. for times ranging from 1 to 11 days. At the end of these periods plates were then washed with medium at 4° C. and gradually warmed to 37° C. in medium containing 10% fetal calf serum. Cells were allowed to recover for 24 hours at 37° C. At the end of this period, cell culture plates were assayed as described previously (5,10) for 1 hour at 37° C. with ALAMAR BLUE™ (AccuMed International, Westlake, Ohio), a non-toxic metabolic indicator. ALAMAR BLUE™ was diluted 1:20 in HBSS without phenol red and 0.5 ml was placed in each cell culture well subsequent to media removal. The metabolic-dependent conversion of the ALAMAR BLUE™ to its fluorescent form was monitored using the CytoFluor 2350 (Millipore Corporation, Bedford, Mass.) or the CytoFluor II (PerSeptive Biosystems, Cambridge, Mass.) with a 530 rim excitation/590 rim emission filter set. After the assay the ALAMAR BLUE™ solution was then removed and replaced with 1.0 ml medium plus 10% fetal calf serum. Cells were then placed back in the incubator at 37° C. They were assayed again every day or every other day in an identical manner with ALAMAR BLUE@. This ALAMAR BLUE™ procedure was repeated in most cases for 4 to 7 days.

Calcein-AM was obtained from Molecular Probes of Eugene, Oreg. and used as a membrane integrity dye. Stock vials of Calcein were reconstituted to 1 mg Calcein-AM/ml DMSO (Sigma). This stock solution was mixed 1/100 with HBSS (GIBCO) and incubated for one hour with MDCK cells that had been cold-stored at 4° C. for either 7 days. The cells were then washed in Hanks Balanced Salt Solution and the retention of the dye in situ was analyzed using the CytoFluor 2350 or the CytoFluor II using a 485 rim excitation/530 emission filter set. The greater the fluorescence units, the more dye was presumed to be retained by the cells.

Cold-storage solutions. HYPOTHERMOSOL® was formulated in our laboratory with the permission of Cryomedical Sciences, Rockville, Md. The complete recipe of this solution has been published (4). EDTA was from Sigma. The Vitamin E (α-tocopherol) and EDTA were obtained from Sigma Chemical Co. The apoptosis protease pan-inhibitors IDUN-1529 and IDUN-1965 were obtained from IDUN pharmaceuticals, San Diego Calif. The apoptosis protease inhibitor, Caspase-1 Inhibitor V was obtained from CalBiochem (La Jolla, Calif.). All stock protease inhibitors were dissolved in DMSO and then subsequently diluted in HYPOTHERMOSOL®. Vitamin E was first dissolved in DMSO (Sigma) before adding to HYPOTHERMOSOL®. VIASPAN® was graciously donated to us by Dr. Anne Robichaud, DuPont Merck Pharmaceutical Company, Wilmington, Del. As per agreement with DuPont-Merck, VIASPAN® was not altered in any manner (such as the addition of EDTA or Vitamin E) for the experiments described herein. All experiments were repeated at least 3 times.

DNA gel electrophoresis. MDCK cells were cold-stored as confluent monolayers in 75 cm² T-flasks (Corning Inc., Corning, N.Y.) for 1 to 6 days at 4° C. in either HYPOTHERMOSOL® or DME. Cell cultures were then brought to 37° C. and the medium replaced as described above. The cells were allowed to recover in cell culture medium at 37° C. Cells that lifted during this recovery period were then rinsed and resuspended in 0.5 ml of STE buffer (8% sucrose, 50 mM Tris-HCl, 50 mM EDTA, pH 8.0) for storage at −70° C. Adherent cells were lifted using trypsin/EDTA and prepared similarly for storage.

After these cells were thawed and pelleted at 500×g in 1.6 ml microfuge tubes, they were resuspended in digestion buffer { 100 mM NaCl, 10 mM Tris-HCl, 25 mM EDTA (pH 8.0), 10% SDS} and triturated using a 1.0 ml syringe equipped with a 26-gauge hypodermic needle. Proteins were precipitated using several phenol-chloroform extractions. Total nucleic acids were precipitated at −20° C. following the addition of 3M sodium acetate and 100% ice cold ethanol to the resulting aqueous phase. The dried nucleic acid pellet was resuspended in 50 mM Tris-HCl (pH 8.0)–0.1% sodium dodecyl sulfate. RNA was degraded through the addition of RNase A (Sigma) at a final concentration of 100 μg/ml and subsequent incubation at 37° C. for at least 30 minutes. Phenol-chloroform extractions were performed until no debris remained at the interface. DNA was precipitated as described previously and resuspended in TE {10 mM Tris-HCl (pH 8.0), 1 mM EDTA}.

Degraded and intact DNA were visualized using standard agarose gel electrophoresis. DNA was separated on 1.5% agarose gels at 90V in TAE buffer {40 mM Tris-acetate, 2 mM EDTA (pH 8.0)}.

Data Analysis

Fluorescence units were converted to percent viability based upon experimental controls. Calculations of standard deviations were performed and statistical significance was determined using ANOVA (Table 1).

Example I

MDCK cells were grown to confluency in 24 well plates. Next, the medium was decanted and either HYPOTHERMOSOL®, HYPOTHERMOSOL® supplemented with 0.1 mM EDTA, HYPOTHERMOSOL® supplemented with 1 mM Vitamin E, VIASPAN® or DME was added to the wells. MDCK cells were then stored at 4° C. for 7 days and allowed to recover for 4 days at 37° C. On each of these 4 days (as well as immediately after removal from the cold, i.e. "0" days) the medium was decanted and the cells incubated for 1 hour at 37° C. in ALAMAR BLUE™. The relative fluorescence levels in each well were quantified using the CytoFluor. The ALAMAR BLUE™ solution on the cells was then decanted, the wells filled with DME with fetal calf serum, and the plates returned to the 37° C. incubator for 24 hours. At the end of this period another ALAMAR BLUE™ assay was carried out. The data depicted in FIG. 1 demonstrate that cells that had been cold-stored in HYPOTHERMOSOL® with Vitamin E or EDTA had higher fluorescence levels than those stored in either the unmodified HYPOTHERMOSOL® or VIASPAN®.

Example II

To determine if ALAMAR BLUE™ was truly reflecting differences in viability, a membrane integrity dye was used in a similar manner. MDCK cells were placed at 4° C. for 7 days in either HYPOTHERMOSOL®, HYPOTHERMOSOL® supplemented with Vitamin E, HYPOTHERMOSOL® supplemented with EDTA or DME. Immediately after moving the cells from the cold to 37° C. the cells were incubated with ALAMAR BLUE™ for 1 hour and the fluorescence quantified using the CytoFluor. Next, all ALAMAR BLUE™® was washed from the cells and the membrane integrity dye, Calcein-AM, was added for 1 hour at 37° C. The unincorporated dye was washed from the cells, replaced with Hanks Balanced Salt Solution, and the resulting fluorescent cells were analyzed in the CytoFluor. The resulting data appear in FIG. 4. Note that the fluorescence levels of ALAMAR BLUE™ mimic the fluorescence levels of Calcein.

Example III

Vitamin E and EDTA were tested to determine if these supplements had additive effects. MDCK cells were cold-stored for 11 days in HYPOTHERMOSOL® with Vitamin E, HYPOTHERMOSOL® with EDTA, HYPOTHERMOSOL® with both Vitamin E and EDTA, or the base HYPOTHERMOSOL®. These variant solutions were compared to cells stored in VIASPAN® or DME. Note that the best performing solution is HYPOTHERMOSOL® with both Vitamin E and EDTA (FIG. 3).

Example IV

MDCK cells stored for 1 or 2 days in DME were allowed to recover for 3 days at 37° C. As a result of cold-storage many cells detached from the substratum and were collected. Their DNA was isolated, and characterized on a DNA gel (FIG. 6, lanes 3 and 4). Cells that remained attached to the substratum after 1 day cold-storage were also collected, their DNA isolated and characterized on a DNA gel (FIG. 6, lane 2). (DNA from attached cells after 1 and 2 days cold storage were similar and only DNA from cells stored in the cold for 1 day is represented here). Note that the DNA in lanes 3 and 4 have a ladder-like appearance, whereas the DNA from attached cells (lane 2) appears intact and exhibits a high molecular weight band indicative of intact genomic DNA.

Example V

A similar protocol was executed with MDCK cells that had been stored in HYPOTHERMOSOL® for 1, 2, 4, 5 and 6 days (FIG. 6, lanes 6–10) and allowed to recover at 37° C. for 3 days. The DNA of the cells that remained attached in cultures stored for 1 day (lane 5) appeared as a single band similar to the cells attached after 2 to 6 days cold-storage (data not shown). The DNA of cells that had lifted, however, have a ladder-like, apoptotic periodicity with bands appearing every 200 bases. There was also a smear at the top of these lanes not evident in intact DNA isolated from adherent cells. The longer the plates were stored at 4° C., the greater the number of cells detached (data not shown). This observation is not apparent in the gels because the same amount of DNA was loaded in each lane in FIG. 4. Note that there is more laddering apparent at earlier times of cold-storage (lanes 6–8) with a DNA smear being predominant at the later storage times (lanes 9–10).

Example VI

The possibility of apoptosis involvement in cell death due to extended cold-storage was explored by adding apoptosis protease inhibitors to HYPOTHERMOSOL®. The apoptosis-specific protease pan-inhibitors IDUN-1529 and IDUN-1965 were added to HYPOTHERMOSOL® and the cells cold-stored for 6 days. No protease inhibitors were present during the recovery period. Note that both IDUN-1529 (100 EM) and IDUN-1965 (100 μM) were able to protect MDCK cells during this period (FIG. 5). An additional apoptosis-specific protease inhibitor, Caspase-1 Inhibitor V, was also tested in a similar manner. The data in FIG. 6 show that the addition of Caspase-1 Inhibitor V improves the cold-storage capability of HYPOTHERMOSOL® in a dose-dependent manner.

Example VII

Experiments were designed using the prostate cancer cell line, PC-3, as an in vitro model to study the effects of temperature on the molecular mechanisms underlying cell death. Confluent PC-3 cultures were exposed to temperatures ranging from 37° C. to −80° C. and allowed to recover for two days. Dead and living cells were isolated and assayed for DNA fragmentation using agarose gel electrophoresis. Cells exposed to temperatures above −5° C. exhibited non-random DNA fragmentation, a characteristic of apoptotic cell death; whereas cells exposed to temperatures below −15° C. died primarily through necrosis as revealed by random DNA fragmentation. Cell viability was then assessed post-cold exposure with the non-invasive, metabolic indicator, ALAMAR BLUE™. Remarkably, an apoptotic inhibitor, IDN-1529, which completely blocked apoptotic DNA laddering following exposure to −10° C. and greater, also partially inhibited cell death in cultures exposed to temperatures ranging from −10 to −75° C. This inhibition occurred even at temperatures at which necrosis appeared to be the primary cause of death. In summary, it is concluded that (1) PC-3 cells can die either by apoptosis or necrosis and the mode of death is determined by the treatment temperature, and (2) apoptotic inhibitors inhibit cell death of PC-3 cells even in regimes that appear to be exclusively necrotic.

Example VIII

A sample experiment illustrating the percent survival of the MDCK cell line 24 hours after thawing from cryostorage in liquid nitrogen (about −196° C.) is depicted in FIG. 12. "Media": control cells maintained at 37° C. in Dulbecco's Minimal Essential Media (DME), an "extracellular-like" media, for a period equivalent to the freezing and thawing interval to which test cells were subjected; DME: cells frozen and thawed in DME culture media with no known cryoprotective functions; DME+5%DMSO: cells frozen and thawed under standard, traditional conditions using DMSO as a cryoprotective agent; DME+10%DMSO: cells frozen and thawed under standard conditions with additional DMSO cryoprotectant; VIASPAN®: cells frozen and thawed in VIASPAN®, an "intracellular-like" commercially available organ maintenance solution used for kidney, liver and pancreas chill preservation (about 0–5° C.); HTS: cells frozen and thawed in HYPOTHERMOSOL® intracellular-like media designed for chill preservation of cells, tissues and organs, offering cryopreservative effects equivalent to the standard media+DMSO, without employing high concentrations of known cryoprotective agents; CRYOSTOR™ CS 5 (HTS+5%DMSO): Cells frozen and thawed in HYPOTHERMOSOL® plus 5%DMSO, wherein DMSO improved cell viability over HTS alone (statistically significant); CRYOSTOR™ CS 10 (HTS+10%DMSO): cells frozen and thawed in HYPOTHERMOSOL® plus 10% DMSO, wherein DMSO unexpectedly improved cell viability over HTS alone (statistically significant); HTS+1 mM CHOLESTEROL: cells frozen and thawed in HYPOTHERMOSOL® plus 1 mM cholesterol, wherein cholesterol, a membrane stabilizing agent, reduces HTS cryoprotection levels; HTS+5 mM VITAMIN E: cells frozen and thawed in HYPOTHERMOSOL® and 5 mM vitamin E, wherein vitamin E, a cell membrane stabilizing agent, enhances HTS cryoprotection levels.

While the invention has been described in detail and with reference to specific embodiments thereof, it will be apparent to those of ordinary skill in the art that various changes and modifications can be made without departing from the spirit and scope of the invention.

All references cited hereinbelow are hereby incorporated herein by reference.

References

1. Southard, J. H.; Belzer, F. O. Organ preservation. Annul Rev. Med. 46: 235; 1995.
2. Pahernik, S. A.; Thasler, W. E.; Mueller-Hoecker, J.; Schildberg, F. W. Hypothermic storage of pig hepatocytes of pig hepatocytes: influence of different storage solutions and cell density. Cryobiology 33: 552; 1996.
3. Fisher, R. L.; Hasal, S. J.; Sanuik, J. T.; Hasal, K. S.; Gandolfi, A. J.; Brendel, K. Cold and cryopreservation of dog liver and kidney slices. Cryobiology 33: 163; 1996.
4. Taylor, M. J.; Bailes, J. E.; Elrifai, A. M.; Shih, T. S.; Teeple, E.; Leavitt, M. L.; Baust, J. G.; Maroon, J. D. A new solution for life without blood: Asanguineous low flow perfusion of a whole-body perfusate during 3 hours of cardiac arrest and profound hypothermia. Circulation 91, 431; 1995.
5. Cook, J. R; Eichelberger, H.; Robert, S.; Rauch, J.; Baust, J. G.; Taylor, M. J.; Van Buskirk, R. G. Cold-storage of synthetic human epidermis in HypoThermosol. Tissue Engineering. 4: 361; 1995.
6. Korbutt, G. S.; Pipeleers, D. G. Cold-preservation of pancreatic beta cells. Cell Transplant. 3: 291; 1994.
7. Rodriguez, J. V.; Mamprin, M. E.; Guibert, E. E.; Labadie, G. Protective effect of glutathione (GSH) over glutathione monoethyl-ester (GSH-E) on cold preservation of isolated rat liver cells. Cell Transplant. 4: 245; 1995.
8. Levi, A. D.; Evans, P. J.; Mackinnon, S. E.; Bunge, R. P. Cold storage of peripheral nerves: an in vitro assay of cell viability and function. Glia 10: 121; 1994.
9. Campion, J. P.; Porchet, N.; Aubert, J. P.; L'Helgoualc'h A.; Clement, B. UW preservation of cultured human gallbladder epithelial cells: phenotypic alterations and differential mucin gene expression in the presence of bile. Hepatology 21: 223; 1995.
10. Van Buskirk, R. G.; Rauch, J.; Robert, S; Taylor, M. J.; Baust, J. G. Assessment of hypothermic storage of normal human epidermal keratinocytes (NHEK) using Alamar Blue. In Vitro Tox. 9(3): 297–303; 1996.
11. Lopukhin, S. Y.; Peek, D. F.; Southard, J. H.; Belzer, F. O. Cold storage of the heart with University of Wisconsin solution and 2,3-butanedione monoxime: Langerdorff vs isolated working rabbit heart model. Cryobiology 33: 178; 1996.
12. Fischer, J. H.; Jeschkeit, S. Effectivity of freshly prepared or refreshed solutions for heart preservation versus commercial EuroCollins, Bretschneider's HTK or University of Wisconsin solution. Transplantation 59: 1259; 1995.
13. Zhang, J.; Furukawa, R. D.; Fremes, S. E. The beneficial effects of heat-shock for prolonged hypothermic storage. J. Surg. Res. 63: 314; 1996
14. den Butter, G.; Marsh, D. C.; Lindell, S. L.; Belzer F. O.; Southard, J. H. Effect of glycine on isolated, perfused rabbit livers following 48 hour preservation in University of Wisconsin solution without glutathione. Transpl. Int. 7: 195; 1994.
15. Todo, S.; Hamada, N.; Zhu, Y.; Zhang, S.; Subbotin, V.; Nemoto, A.; Takeyoshi, Il; Starzl, T. E. Lazaroid U-74389G for 48-hour canine liver preservation. Transplantation 61: 189; 1996.
16. Minor, T.; Yamaguchi, T.; Isselhard, W. Effects of taurine on liver preservation in UW solution with consecutive ischemic rewarming in the isolated perfused rat liver. Transpl. Int. 8: 174; 1995
17. Carbognani, P.; Spaggiari, L.; Cattelani, R.M.; Dell'Abate, P.; Soliani, P.; Grandi, D.; Bobbio, P. Ultrastructural damage of the pulmonary endothelial cell after storage in lung preservation solutions. Comparison between Belzer and Euro-Collins solutions. J. Cardiovasc. Surg. 36: 93; 1995
18. Alessandrini, F.; Sasaki, S.; Said, S. I.; Lodi, R.; LoCicero, J. Enhancement of extended lung preservation with a vasoactive intestinal peptide-enriched University of Wisconsin solution. Transplantation 59: 1253; 1995.
19. Bryan, C. L.; Patefield, A. J.; Cohen, D.; Nielsen, J. L.; Emanuel, B.; Calhoon, J. H. Assessment of injury in transplanted and nontransplanted lungs after 6 h of cold storage with glutathione. J. Appl. Physiol. 76: 1232; 1994.
20. McAnulty, J. F.; Huang, X. Q. The effect of simple hypothermic preservation with Trolox and ascorbate on lipid peroxidation in dog kidneys. Cryobiology 33: 217; 1996.
21. Katz, S. M.; Sun, S.; Schechner, R. S.; Tellis, V. A.; Alt, E. R.; Greenstein, S. M. Improved small intestinal preservation after lazaroid U74389G treatment and cold storage in University of Wisconsin solution. Transplantation 59: 694; 1995.
22. Heales, S. J.; Bolanos, J. P.; Land, J. M.; Clark, J. B. Trolox protects mitochondrial complex IV from nitric oxide-mediated damage in astrocytes. Brain Res 68: 243; 1994.
23. McClain, D. E.; Kalinich, J. F.; Ramakrishnan, N. Trolox inhibits apoptosis in irradiated MOLT-4 lymphocytes. FASEB 9: 1345; 1995.
24. Kerr, J. R.; Winterford, C. M.; Harmon, B. V. Apoptosis. Its significance in cancer and cancer therapy. Cancer 73: 2013; 1994.
25. Hirsch, T.; Marchetti, P.; Susin, S. A.; Dallaporta, B.; Zamzami, N.; Marzo, I.; Geuskens, M.; Kroemer, G. The apoptosis-necrosis paradox. Apoptogenic proteases activated after mitochondria permeability transition determine the mode of cell death. Oncogene 15: 1573; 1997.
26. Adams, R. M.; Wang, M.; Crane, A. M., et al. Effective cryopreservation and long-term storage of primary human hepatocytes with recovery of viability, differentiation, and replicative potential. Cell Transplantation. 4: 579–586; 1995.
27. Chesne, C.; Claire, G.; Fauntrel, A., et al. Viability and function in primary culture of adult hepatocytes from various animal species in human beings after cryopreservation. Hepatology. 18: 406–414; 1993.
28. Cotter, T. G. Programmed to die—the genetic regulation of cell death and its implications. BIOforum International. 1: 8–11; 1997.
29. Coundouris, J. A.; Grant, M. H.; Engeset, J., et al. Cryopreservation of human adult hepatocytes for use in drug metabolism and toxicity studies. Xenobiotica. 23: 1399–1409; 1993.
30. Cheng, Y. et al. Caspase inhibitor affords neuroprotection with delayed administration in a rat model of neonatal hypoxic-ischemic brain injury. J. Clinical Invest. 101: 1992–1997; 1998.
31. Evan, G.; Littlewood, T. Apoptosis: A matter of life and cell death. Science. 281: 1317–1322; 1998.

32. Fischlein, T.; Schutz, A.; Uhlig, A., et al. Integrity and viability of homograft valves. Euro. J. Carido-Thorac Surgery. 8(8): 425–430; 1994.
33. Freshney, R. I. Culture of animal cells: A manual of basic techniques, Third Edition. New York: Wiley-Liss; 1994: 287–307.
34. Gao, D. Y.; Mazur, P.; Critser, J. K. Fundamental cryobiology of mammalian spermatozoa. In: Karow, A. M.; Critser, J. K., eds. Reproductive Tissue Banking. New York: Academic Press; 1997: 263–328.
35. Green, D. R; Reed, J. C. Apoptosis: Mitochondria and apoptosis. Science. 281: 13091316; 1998.
36. Hollister, W. R.; Mathew, A. J.; Baust. J. G., et al. The effects of freezing on cell viability and mechanisms of cell death in an in vitro human prostate cancer cell line. Molecular Urology: A Transnational Approach 2(1): 13–18; 1998.
37. Kerr, J. F. R.; Wyllie, A. H.; Currie, A. R. Apoptosis: A basic biological phenomenon with wide-ranging implications in tissue kinetics. Br. J. Cancer. 26: 239–247; 1972.
38. Langer, R; Yacanti, J. P. Tissue Engineering. Science. 260: 920–926; 1993.
39. Mathew, A.; Baust, J. G.; Van Buskirk, R. G. Optimization of HypoThermosol® for the hypothermic storage of cardiomyocytes—Addition of EDTA. In Vitro Toxicology. 10(4): 407–415; 1997.
40. Nagle, W. A.; Soloff, B. L.; Moss, A. J., et al. Cultured Chinese hamster cells undergo apoptosis after exposure to cold but nonfreezing temperatures. Cryobiology. 27: 439–451; 1990.
41. Neronov, A. J.; Bratanov, M. B.; Tsenov, I. A. Cryopreservation of myeloma cells, hybridoma cells, and lymphocytes with different cryoprotectants. Cryobiology, 29(2): 296–299; 1992.
42. Parks, J. E. Hypothermia and mammalian gametes. In: Karow, A. M.; Critser, J. K., eds. Reproductive Tissue Banking. New York: Academic Press; 1997: 229–261.
43. Paynter, S.; Cooper, A.; Thomas, N., et al. Cryopreservation of multi-cellular embryos and reproductive tissues. In: Karrow, A M.; Critser, J. K., eds. Reproductive Tissue Banking. New York: Academic Press; 1997: 359–393.
44. Polge, C.; Smith, A. U.; Parkes, A. S. Revival of spermatozoa after vitrification and dehydration at low temperatures. Nature. 164: 666; 1949.
45. Rowe, A. W. Cryopreservation of blood—an historical perspective. Infusionsther Transfusionsmed. 22: 36–40; 1995.
46. Taylor, M. J.; Elrafai A. M.; Bailes, J. E. Hypothermia in relation to the acceptable limits of ischemia for bloodless surgery. Advances in Low Temperature Biology. 3: 1–64; 1996.
47. Thomberry, N. A.; Lazenboik, Y. Caspeses: Enemies within. Sciences. 281: 1312–1316; 1998.
48. Voytik-Harbin, S. L.; Brigh®an, A. O.; Waisner, B., et al. Application and evaluation of the alamarBlue® g assay for cell growth and survival of fibroblasts. In Vitro Cellular & Developmental Biology 34(3): 239–246; 1998.

What is claimed is:

1. A cell-free solution composition for hypothermic storage of animal or human organs, tissues or cells, the cell-free solution comprising:
   (a) one or more electrolytes selected from the group consisting of potassium ions at a concentration ranging from 35–45 mM, sodium ions ranging from 80–120 mM, magnesium ions ranging from 2–10 mM, and calcium ions ranging from 0.01–0.1 mM;
   (b) a macromolecular oncotic agent having a size sufficiently large to limit escape from the circulation system and effective to maintain oncotic pressure equivalent to that of blood plasma and selected from the group consisting of human serum albumin, polysaccharide and colloidal starch;
   (c) a biological pH buffer effective under physiological and hypothermic conditions;
   (d) a nutritive effective amount of at least one simple sugar;
   (e) an impermeant and hydroxyl radical scavenging effective amount of mannitol;
   (f) an impermeant anion impermeable to cell membranes and effective to counteract cell swelling during cold exposure, said impermeant ion being at least one member selected from the group consisting of lactobionate, gluconate, citrate and glycerophosphate;
   (g) a substrate effective for the regeneration of ATP, said substrate being at least one member selected from the group consisting of adenosine, fructose, ribose and adenine, and
   (h) at least one agent which regulates apoptotic induced cell death.

2. A cell-free solution composition for hypothermic storage of animal or human organs, tissues or cells according to claim 1 further comprising glutathione.

3. A cell-free solution composition for hypothermic storage of animal or human organs, tissues or cells according to claim 1,
   wherein the at least one agent which regulates apoptotic induced cell death is a comprises an agent which reduces cellular levels of free radicals.

4. A cell-free solution composition for hypothermic storage of animal or human organs, tissues or cells according to claim 2,
   wherein the at least one agent which reduces cellular levels of free radicals comprises a member selected from the group consisting of vitamin E and EDTA.

5. A cell-free solution composition for hypothermic storage of animal or human organs, tissues or cells according to claim 1,
   wherein the hypothermic storage occurs between about 10° C. and 0° C.

6. A cell-free solution composition for hypothermic storage of animal or human organs, tissues or cells according to claim 5,
   wherein the agent which regulates apoptotic induced cell death comprises an inhibitor of one or more caspase proteases.

7. A cell-free solution composition for hypothermic storage of animal or human organs, tissues or cells according to claim 1,
   wherein the hypothermic storage is cryostorage between a temperature at which the onset of freezing occurs to −196° C.

8. A cell-free solution composition for hypothermic storage of animal or human organs, tissues or cells according to claim 7,
   wherein the agent which regulates apoptotic induced cell death comprises an inhibitor of one or more caspase proteases.

9. A method of storing of animal or human tissues or cells at a hypothermic temperature comprising:

(a) combining cells with a cell-free solution composition for hypothermic storage having at least one agent which regulates apoptotic induced cell death and (b) chilling cells to between about 10° C. and 0° C.

10. A method of storing animal or human cells at a hypothermic temperature according to claim 9, wherein the at least one agent which regulates apoptotic induced cell death comprises an agent which regulates nitrous oxide synthtase activity.

11. A method of storing animal or human cells at a hypothermic temperature comprising:

(a) combining cells with a cell-free solution composition for hypothermic storage having at least one agent which regulates apoptotic induced cell death, and (b) chilling cells to between the temperature at which the onset of freezing occurs to −196° C.

12. A method of storing animal or human cells at a hypothermic temperature according to claim 11, wherein the at least one agent which regulates apoptotic induced cell death comprises an agent which regulates nitrous oxide synthtase activity.

* * * * *

UNITED STATES PATENT AND TRADEMARK OFFICE
CERTIFICATE OF CORRECTION

PATENT NO.   : 6,045,990
DATED        : April 4, 2000
INVENTOR(S)  : Baust et al.

It is certified that error appears in the above-identified patent and that said Letters Patent is hereby corrected as shown below:

<u>Title page,</u>
Item [76], Inventors: change "Mathew Aby" to -- Aby Mathew --.

Signed and Sealed this

Tenth Day of September, 2002

Attest:

JAMES E. ROGAN
Attesting Officer          Director of the United States Patent and Trademark Office